(12) United States Patent
Thompson et al.

(10) Patent No.: US 7,737,306 B2
(45) Date of Patent: Jun. 15, 2010

(54) SYNTHETIC NAVEL ORANGEWORM PHEROMONE COMPOSITION AND METHODS RELATING TO PRODUCTION OF SAME

(75) Inventors: Andrew Thompson, Mountainside, NJ (US); Shawn Zhang, Stirling, NJ (US); Lonnie Robarge, Seattle, WA (US)

(73) Assignee: Suterra, LLC, Los Angeles, CA (US)

( * ) Notice: Subject to any disclaimer, the term of this patent is extended or adjusted under 35 U.S.C. 154(b) by 0 days.

(21) Appl. No.: 12/255,951

(22) Filed: Oct. 22, 2008

(65) Prior Publication Data

US 2010/0099920 A1    Apr. 22, 2010

(51) Int. Cl.
 C07C 45/00     (2006.01)
(52) U.S. Cl. ........................... 568/486; 568/488
(58) Field of Classification Search ............... 568/486, 568/488
 See application file for complete search history.

(56) References Cited

U.S. PATENT DOCUMENTS

| | | | |
|---|---|---|---|
| 4,070,184 A | | 1/1978 | Scheithauer, Jr. et al. |
| 4,198,533 A | * | 4/1980 | Carney et al. ............... 568/840 |
| 4,228,093 A | | 10/1980 | Carney et al. |
| 4,400,550 A | * | 8/1983 | Bishop et al. ............... 568/486 |
| 4,760,196 A | | 7/1988 | Fukumoto et al. |
| 4,912,253 A | | 3/1990 | Fukumoto et al. |
| 4,918,252 A | | 4/1990 | Fukumoto et al. |
| 4,979,673 A | | 12/1990 | Wilk et al. |
| 5,082,961 A | | 1/1992 | Fukumoto et al. |
| 5,162,596 A | | 11/1992 | Fukumoto et al. |
| 5,292,973 A | | 3/1994 | Fukumoto et al. |
| 5,463,149 A | | 10/1995 | Fukumoto et al. |
| 5,481,040 A | | 1/1996 | Fukumoto et al. |
| 5,532,421 A | | 7/1996 | Terauchi et al. |
| 5,714,649 A | | 2/1998 | Fukumoto et al. |
| 5,814,326 A | | 9/1998 | Senda et al. |
| 5,880,318 A | | 3/1999 | Fukumoto et al. |
| 6,001,346 A | | 12/1999 | Delwiche et al. |
| 6,264,939 B1 | | 7/2001 | Light et al. |
| 6,451,417 B1 | | 9/2002 | Sumi et al. |
| 6,521,224 B1 | | 2/2003 | Ogura et al. |
| 6,562,331 B1 | | 5/2003 | Ito et al. |
| 6,599,500 B1 | | 7/2003 | Ogawa et al. |
| 6,986,854 B2 | | 1/2006 | Sumit et al. |
| 2006/0110420 A1 | | 5/2006 | Leal |
| 2006/0280765 A1 | | 12/2006 | Kuenen et al. |

OTHER PUBLICATIONS

Sonnet al. Stereospecific Synthesis of (Z,Z)-11, 13-hexadecadienal. A Female Sex Pheremone of the Navel Orangeworm. Journal of Chemical Ecology, 1980, vol. 6 (1), 221-228.*
Johnson JA; Survival of indianmeal moth and navel orangeworm (Lepidoptera: Pyralidae) at low temperatures. J Econ Entomol. Aug. 2007;100(4):1482-8.
Burks CS, Brandl DG. Seasonal abundance of the navel orangeworm, Amyelois transitella, in figs and the effect of peripheral aerosol dispensers on sexual communication. J Insect Sci. 2004;4:40. Epub Dec. 6, 2004.
Girling RD, Cardé RT. Analysis of the Courtship Behavior of the Navel Orangeworm, Amyelois transitella (Walker) (Lepidoptera: Pyralidae), with a Commentary on Methods for the Analysis of Sequences of Behavioral Transitions; Journal of Insect Behavior. 2006 19(4):497-520. (published online Sep. 2006).
Parra-Pedrazzoli AL, Leal WS. Sexual behavior of the navel orangeworm, Amyelois transitella (Walker) (Lepidoptera: Pyralidae). Neotrop Entomol. Nov.-Dec. 2006;35(6):769-74.
Stelinski LL Gut LJ, Haas M, McGhee P, Epstein D. Evaluation of aerosol devices for simultaneous disruption of sex pheromone communication in Cydia pomonella and Grapholita molesta (Lepidoptera: Tortricidae). J Pest Science. 2007; 80(4):225-233.
Suckling DM, Daly JM, Chen X, Karg G. Field electroantennogram and trap assessments of aerosol pheromone dispensers for disrupting mating in Epiphyas postvittana. Pest Management Science. 2006; 63(2):202-209.
Knight AL. Influence of Within-Orchard Trap Placement on Catch of Codling Moth (Lepidoptera: Tortricidae) in Sex Pheromone—Treated Orchards. Environmental Entomol. 2007; 36(2): 425-432.
Leal WS, Parra-Pedrazzoli AL, Kaissling KE, Morgan TI, Zalom FG, Pesak DJ, Dundulis EA, Burks CS, Higbee BS. Unusual pheromone chemistry in the navel orangeworm: novel sex attractants and a behavioral antagonist. Naturwissenschaften. Mar. 2005;92(3):139-46. Epub Jan. 25, 2005.
Shorey HH, Gerber RG. Use of puffers for disruption of sex pheromone communication of Codling Moths (Lepidoptera: Tortricidae) in Walnut Orchards. Environ Entomol. 1996; 25(6):1398-1400.
Shorey HH, Gerber RG. Disruption of Pheromone Communication through the Use of Puffers for Control of Beet Armyworm (Lepidoptera: Noctuidae) in Tomatoes. Environmental Entomology 1996; 55(6):1401-1405.
Siegel, J.P., Kuenen, L.P., Higbee, B.S., Bettiga, J. 2007. Use of nematodes and insecticides for postharvest control of navel orangeworm (Amyelois transitella). California Pistachio Commission Production Research Report. p. 193-198.
Leal, W.S., Kaissling, K.E., Single-sensillum Recording (SSR) from the Navel Orangeworm Male Antennae, Executive Summary, Dec. 10, 2004.
Siegel, J.P., Kuenen, L.P., Higbee, B.S., Bettiga, J. 2007. Determination of the development rate of navel orangeworm (Amyelois transitella)in pistachios and assessment of population structure and winter mortality. California Pistachio Commission Production Research Report. p. 37-44.

(Continued)

Primary Examiner—Sikarl A Witherspoon
(74) Attorney, Agent, or Firm—Dalina Law Group, P.C.

(57) ABSTRACT

One or more embodiments of the invention are directed to the synthetic methods for making lepidopteran pheromones including navel orangeworm pheromones. The synthetic methods involve novel, efficient, and environmentally benign steps and procedures.

27 Claims, 7 Drawing Sheets

OTHER PUBLICATIONS

Burks, C. S., Higbee, B.S., Brandl D.G. 2006. Effect of sanitation on navel orangeworm abundance in and damage to pistachios. California Pistachio Commission Production Research Report. pp. 83-90.

Mohammad Bari, M.A. 2007. Field Evaluation of Integrated Mating Disruption Technique Using 'Suttera Puffers® APM' for the Suppression of the Primary Pest of Artichokes, The Artichoke Plume Moth, Platyptilia Carduidactyla (Riley) . Acta Hort. (ISHS) 730:419-425.

Epstein DL, Stelinski LL, Reed TP, Miller Jr, Gut LJ. Higher Densities of Distributed Pheromone Sources Provide Disruption of Codling Moth (Lepidoptera: Tortricidae) Superior to That of Lower Densities of Clumped Sources. J Econ Entomol. 2007; 99(4): 1327-1333.

Marti S, Zaragoza A, Larsen T; Mating disruption of codling moth, Cydia pomonella (L.), using Puffer® CM, on pome fruit orchards. International Pest Control. 2006; 48:231-236.

Millar, J. G., Kuenen, L. P. Field and Laboratory Studies to Improve Pheromone of Navel Orangeworm, California Pistachio Commission, Project Report: 2003.

Siegel J, Kunen L, Higbee B. Alternatives to Chemical Control for Stored Product and Quarantine Pests of Fresh/dried Fruits and Nuts. California Agriculture—Sep. 21, 2007.

Leal, W.S., Parra-Pedrazzoli, A.L., Ishida, Y., Xu, W., Chen, A., Zalom, F. Pesak, D.J., Dundulis, E.A., Burks, C. S., Higbee, B. Molecular-based Screening of Attractants for the Navel Orangeworm to Improve Trap Catches and Potential for Control (Year-3 Report), Executive Summary 2006 Report.

Shorey HH, Gerber RG. Use of puffers for disruption of sex pheromone communication among navel orangeworm moths (Lepidoptera: Pyralidae) in almonds, pistachios, and walnuts. Environ Entomol. 1996; 25(5):1154-1157.

Burks, C., Higbee, B., Brandi, D. NOW Mating Disruption, Dispersal, and Damage Prediction, Almond Board of California, Conference Proceedings 2006.

Burks, C., Higbee, B. Daane, K., Bentley, K. Mating Disruption for Suppression of Navel Orangewomn Damage in Almonds, 2003.

Burks, C., Higbee, B. Daane, K., Bentley, K., Kuenen, B. Mating Disruption for Suppression of Navel Orangeworm Damage in Almonds, 2004.

Burks, C., Higbee, B. Brandl, D. Mating Disruption for Suppression of Navel Orangeworm Damage in Almonds, 2005.

Burks, C., Higbee, B. Daane, K., Bentley, K., L.P.S. Kuenen, Mating Disruption for Suppression of Navel Orangeworm Damage in Pistachios (Year 1), 2003.

* cited by examiner

SYNTHETIC NAVEL ORANGEWORM PHEROMONE COMPOSITION AND METHODS RELATING TO PRODUCTION OF SAME

BACKGROUND OF THE INVENTION

1. Field of the Invention

One or more embodiments of the invention relate to compositions and method for synthesizing the navel orangeworm pheromones and methods for using thereof for pest management.

2. Description of the Related Art

As the need for food production in the world grows so does the need for new forms of pest control. The increasing use of conventional pesticides leads to resistant pests, severely alters the natural ecology, and damages the environment. This problem has led to innovative ways in pest management without the use of pesticides. One of the ways that has been presented is the use of insect sex pheromones (Shani, A., "Integrated pest management using pheromones," *Chemtech* 28(3), pp. 30-35 (1998)).

Sex pheromones are used in the chemical communication of many insects for attracting the species of the opposite sex to engage in reproduction. Pheromones are useful for pest control largely through four means: monitoring, mass trappings, attract and kill, and disruption of communication or confusion. "Monitoring" methodology attracts the pests to a central area, which allows the grower to obtain precise information on the size of the pest population in order to make informed decisions on pesticide use or non-use. "Mass trappings" brings the pest to a common area and physically trap them, which hinder production of new generations of pests. "Attract and kill" allows the pests to be drawn into a centrally located container and killed in the container by the pesticide reducing the need to spread pesticides in broad areas. "Disruption of communication" can occur in that a large concentration of sex pheromone can mask naturally occurring pheromones or saturate the receptors in the insect causing confusion and disruption of natural reproductive means (Shani, 1998). For each one of these means, each individual species of pest needs to be treated with a tailor-made composition which can add substantially to the cost in creating a bulk amount.

Pheromones are considered relatively non-toxic, not environmentally persistent (decompose quickly in nature), and do not create resistance by pests. These qualities make them a superior choice as an alternative to pesticides. Because of the need for more environmentally friendly pest management, the industry has emphasis to develop more efficient and cost-effective production methods for the pheromones while utilizing more environmentally benign methods for their production.

One of the more pervasive pests in agriculture areas of tree-nut production is the larval worm of the moth family Lepidoptera: class Pyralidae known as the Navel Orangeworm, *Amyelosis transitella*. The tree-nut industry is a multi-billion dollar industry but estimates show only 1% of the cultivated land uses pheromones for pest control (Shani, 1998). With a relatively high cost for producing the pheromones, the economic impact creates a strong need to create an efficient method to produce the sex pheromone of the navel orangeworm.

One of the major sex pheromone of the navel orangeworm has been isolated and analyzed is (Z,Z)-11,13-hexadecadienal (HDAL). This pheromone and others have been described in studies and belongs in the Ando type I pheromones (Ando T. et al., "Lepidopteran sex pheromones," *Top Curr Chem* 239: 51-96, 2004). HDAL has been shown in other studies to have a high affinity for binding to a major pheromone binding protein (AtraPBP) which can correlate to having some effect on the mating disruption and monitoring of the adult moths (Leal et al., "Unusual pheromone chemistry in the navel orangeworm: novel sex attractants and a behavioral antagonist," *Naturewissenshaften* 92:139-146 (2005)).

A method of synthesis for HDAL was described in a 1980 publication that described an at least seven step method (Sonnett, P. E. and R. R. Heath, "Stereospecific synthesis of (Z,Z)-11,13-hexadienal, a Female Sex Pheromone of the Navel Orangeworm, *Amyelosis transitella*, (Lepidoptera:Pyralidae)" *Journal of Chemical Ecology*, 6,221-228, 1980). U.S. Pat. Nos. 4,198,533 and 4,228,093 describe similar seven or more reaction step methods. Some of the problems faced by industry in the process of making pheromones, include use of toxic reagents, lack of available refined starting materials on the market, and inefficiencies in the processes. There is need for new and better methods for synthesizing the navel orangeworm pheromones.

To the best of knowledge known at the time of the patent application, the improved methods herein for creating a synthetic composition of the navel orangeworm pheromone for use in pest management have not been described.

BRIEF SUMMARY OF THE INVENTION

One or more embodiments of the present invention are novel and improved methods for synthesizing a sex pheromone of the navel orangeworm using a reduced number of the presently used seven synthetic steps. Among other benefits these novel pheromone synthetic routes have improved stability of reactants and intermediates.

Accordingly one or more embodiments of the invention provide methods for forming various intermediates and final products including a starting material such as a halo substituted alkyl alcohol. From this starting material, a step includes forming a halo substituted alkanal. Another step includes forming a halo substituted dialkoxy substituted alkyl. Another step includes forming a dialkyloxy substituted alkynyl. Yet another step includes forming a halo substituted alkynyl. Another step includes forming dialkoxy substituted diynyl. A final step includes forming the final pheromone.

In other embodiments of the invention provides for methods of reacting the intermediate products to form the final pheromone product. The step on the starting material is an oxidation to form the next intermediate product. Another step is an O-alkyl-C-alkoxy addition that forms the next intermediate product. Another step is an alkynyl-de-halogenation to form the next intermediate product. Yet another step is a halogenation to form the next intermediate product. Another step is performing a cycle of oxidative addition and reductive elimination to form the next intermediate product. And the final step is a reduction and hydrolysis to form the cis-cis isomer of the pheromone.

Other embodiments of the invention provide for methods of forming the (Z,Z)-11,13-hexadecadienal, utilizing intermediate products in less than seven steps. The starting material in this embodiment utilizes 10-chlorodecan-1-ol. The next step utilizes 10-chlorondecanal. Another step utilizes 10-chloro-1,1-diethoxydecane. Another step utilizes but-1-yne. Yet another step utilizes both 12,12-diethoxydodec-1-yne and 1-bromobut-1-yne. Another step utilizes 16,16-diethoxyhexadeca-3,5-diyne to form the final pheromone.

Other embodiments of the invention provide for methods of forming the (Z,Z)-11,13-hexadecadienal utilizing various reagents. Accordingly, these reagents sodium bromide, sodium acetate, 2,2,6,6-tetramethylpiperidinooxy (TEMPO), ethyl acetate, and sodium hypochlorite are used on the starting material for the first step. The next step utilizes p-toluenesulfonic acid monohydrate and triethylorthoformate to form the next intermediate product. Another step utilizes reagents lithium acetylide, ethylenediamine complex and sodium iodide in dimethylsulfoxide to form another intermediate product. Another step utilizes reagents potassium hydroxide in water additionally with bromide to form a reactant. Yet another step includes hydroxylamine hydrochloride, copper (I) chloride in methanol and added to with n-propylamine to form yet another intermediate product. And the final step utilizes reagents of cyclohexene and borane-N,N-diethylaniline complex (DEANB) in tetrahydrofuran, glacial acetic acid and either aqueous sulfuric acid or metal tetrafluorborate complexes.

Other embodiments of the invention provide for forming the stable version of the navel orangeworm pheromone (Z,Z)-11,13-hexadecadienal by utilizing a method of less than six synthetic steps. Similarly, the embodiment provides a method for performing an oxidation on a starting material preferably 10-chlorodecan-1-ol to form the aldehyde. Another step protects the aldehyde by utilizing a C-alkyoxy O-alkyl addition procedure. From this intermediate product, the compound is reacted with a terminal alkyne preferably 1,3-hexadiyne that was optionally formed from an internal alkyne such as 2,4-hexadiyne by use of a nucleophilic addition to form the next intermediate product, 16,16-diethoxyhexadeca-3,5-diyne. This compound then undergoes a further reaction in the method to stereospecifically reduce the diyne moiety and de-protect the aldehyde to create the final pheromone. It is contemplated not using the optional step of forming the terminal alkyne but utilizing a commercially available compound allowing for a method of less than five synthetic steps.

The embodiments of the invention provide for steps utilizing reagents of alkali metal amides such as sodium amide in an ether to optionally rearrange the internal alkyne to a terminal alkyne and to form the next intermediate product.

Another embodiment of the invention provide for a synthesis kit that utilizes all synthetic reagents, starting materials, methods, and apparatuses for forming the (Z,Z)-11,13-hexadecadienal, navel orangeworm sex pheromone.

These and other embodiments of the present invention will readily occur to those of ordinary skill in the art in view of this disclosure.

BRIEF DESCRIPTION OF THE DRAWINGS

The above and other aspects, features and advantages of the invention will be more apparent from the following more particular description thereof, presented in conjunction with the following drawings wherein:

FIG. 2 is the outlined reaction scheme of the synthetic method shown in FIG. 1 Pathway I also named Scheme 1a.

DETAILED DESCRIPTION

Figure 1:
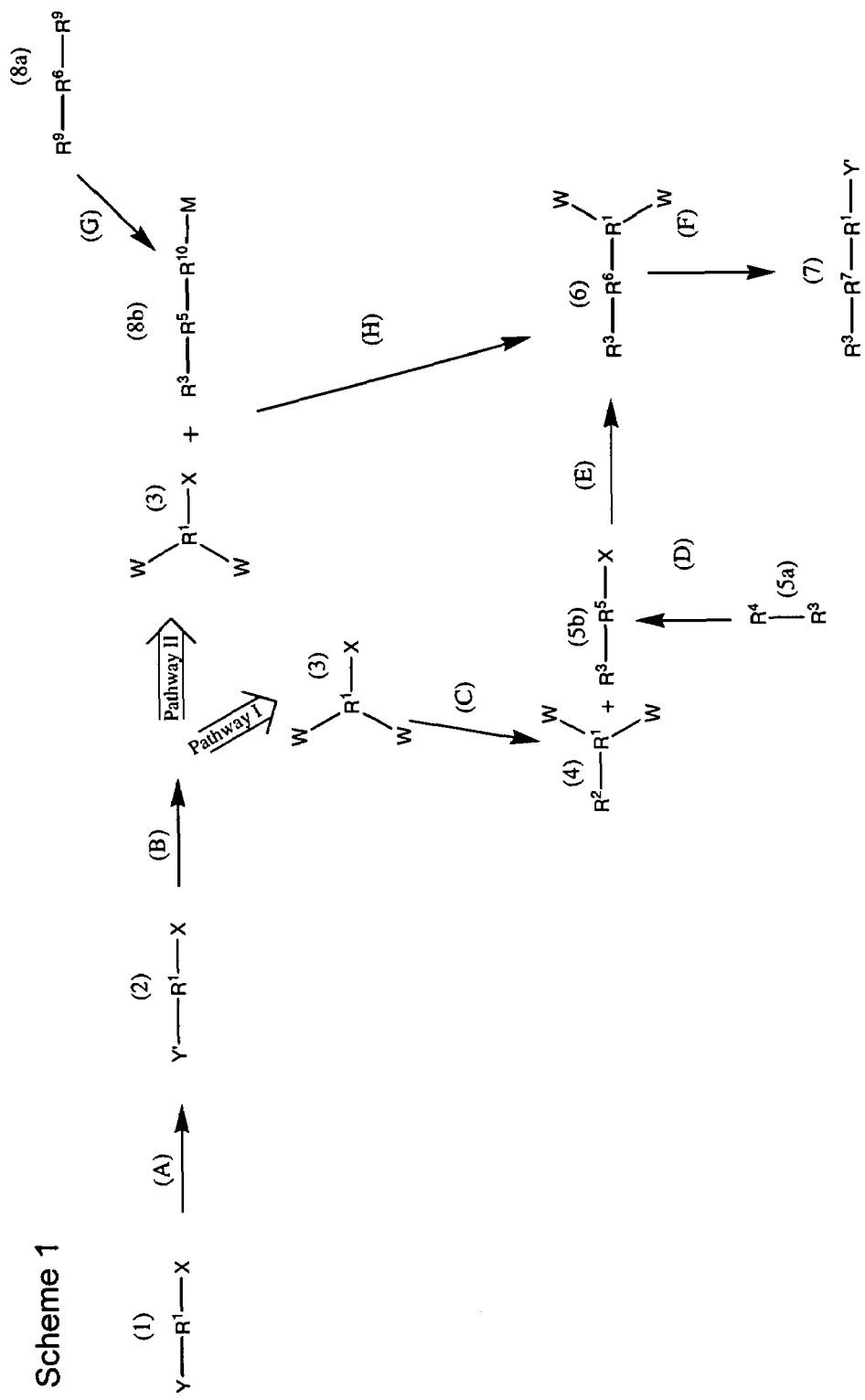
FIG. 1 is the outlined reaction scheme of the synthetic method for making the navel orangeworm sex pheromone. After step B, the reaction scheme diverges into two alternative pathways. The numbers in parentheses designate the formula directly adjacent to it. The letters in parentheses designate the reaction step to which the arrows connote.

A synthetic pheromone composition will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

The practice of the present invention will employ unless otherwise indicated conventional methods of chemistry within the skill of the art. Such techniques, methods, reactions, and the like are explained fully in the literature such as Advanced Organic Chemistry: Reactions, Mechanisms, and structure, Ed. Jerry March 4th ed. (New York, John Wiley and sons, 1985) and Techniques and Experiments for Organic Chemistry, Addison Ault, 5th ed. (University press, 1998).

All publications and patents and patent applications cited herein are hereby incorporated by reference in their entirety.

As used in this specification and in the appended claims, the singular forms "a," "an" and "the" include plural references unless the content clearly dictates otherwise.

The use of the word "preferably" in its various forms is for ease of reading and should not be used to read into the claims anything more.

In describing the invention and embodiments, the following terms will be employed and are intended to be defined as indicated below. If any terms are not fully defined, then the normal usage as used in the art will fill any gaps in the understanding of the terminology.

The term "substitution" is a replacement of an atom or group of atoms in a moiety by another atom or group of atoms.

The term "substituted" means that the specified group or moiety bears one or more substituents. The term "unsubstituted" means that the specified group bears no substituents. The term "optionally substituted" means that the specified group is unsubstituted or substituted by one or more substituents. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a terminal ethyl group is substituted with one additional substituent, one of ordinary skill in the art would understand that such a group has 4 open positions left on carbon atoms. (8 initial positions, minus two for the C—C bond, minus one to which the remainder of the compound is bonded, minus an additional substituent, to leave 4 open positions). Similarly, if an ethyl group in the present compounds is said to be "disubstituted," one of ordinary skill in the art would understand it to mean that the terminal ethyl group has 3 open positions left on the carbon atoms.

The term "reduction" is when a reductant or atom gains an electron, though there may be no shift of electrons, to decrease the oxidation content of the final product or atom. For example in a simple reaction:

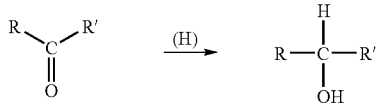

in this example R and R' are alkyl, and H is a generalized reducing agent.

The term "oxidation" is when an oxidant or atom loses an electron, though there may be no shift of electrons, to increase the oxidation content of the final product or atom. For example in a simple reaction:

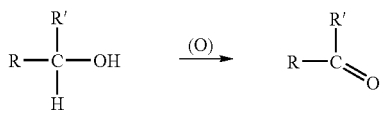

in this example R and R' are alkyl and O is a generalized oxidizing agent.

The term "TEMPO oxidation" is utilizing 2,2,6,6-Tetramethylpiperidinyloxy as a stable nitroxyl radical, which serves in an oxidation reaction as a catalyst. It allows for environmentally benign reactions that are good alternatives to chromium based reagents. An example of a TEMPO oxidation would be the catalyst mixed with a starting material with a metal halide, metal acetate, and metal halogenate kept at controlled concentrations and stirred at a temperature lower than ambient for less than 3 h.

The term "halogenation" is a reaction of an alkyl group with molecular halogen. A hydrogen atom in the alkyl group is substituted by a halogen atom. Reversing the substitution to replace the halogen with a hydrogen or a moiety of a carbon-alkyl group is termed "de-halogenation." For halogenation example in simple reaction:

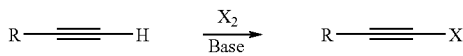

For this example R is alkyl group and X is halogen.

For a de-halogenation (Alkyl de-halogenation) example:

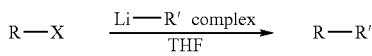

For this example R and R' are alkyl groups and X is halogen.

The named "Cadiot Chodkiewicz" reaction utilizes a copper (I)-catalyzed coupling of a terminal alkyne and an alkynyl halide which offers access to an unsymmetircial diynyl (Cadiot, P.; Chodkiewicz, W. *Chemistry of Acetylenes*; Viehe, H. G., Ed.; Marcel Dekker: New York, 1969; pp 597-647). An example of the reaction is in this simple scheme:

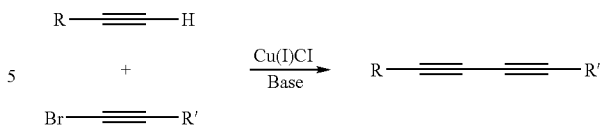

In this example R and R' are Alkyl groups.

Figure 6:
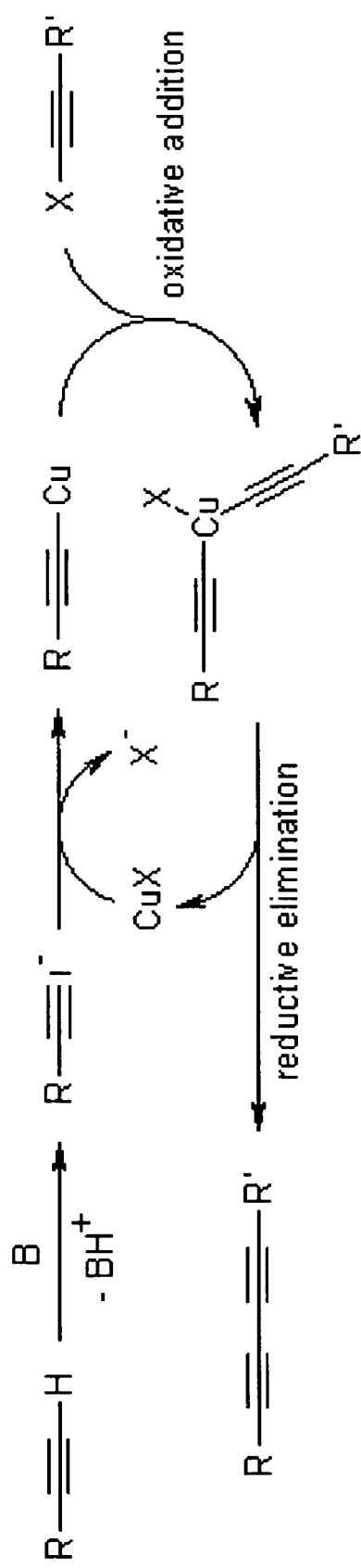
FIG. 6 is a schematic diagram of an oxidative addition and reductive elimination reaction.

The term "oxidative addition" is used in transitional metals catalyzed, organometallic reactions when there is an addition of a sigma bond to a metal. The oxidation state of the metal changes +2. See FIG. 6 for a schematic example. In this example R and R' are alkyl groups, and X is a halogen.

The term "reductive elimination" used in transitional metals catalyzed, organometallic reactions is the reverse of oxidative addition where there is a disassociation of a sigma bond to reform the original organometallic complex. The oxidation state of the metal changes −2. See FIG. 6 for a schematic example. In this example R and R' are alkyl groups, and X is a halogen.

The term "addition" is used referring to an unsaturated molecule with a double bond which can undergo a reaction whereby a pair of electrons is removed from the double bond (for example) and is used to attach new groups to the molecule. For example, an O-Alkyl-C-alkoxy addition transforms the aldehyde into an acetal (also called herein an acetalization) as in this simple example:

In this example R and R' are Alkyl groups.

The term "nucleophilic addition" is an addition reaction wherein a chemical compound a π bond is removed by the creation of two new covalent bonds by the addition of a nucleophile. The nucleophile can be an anion or free electrons seeking an electrophile such as a proton. For example: R—C≡C—C≡C—H+NaNH$_2$→R—C≡C—C≡C: $^{(-)}$Na$^{(+)}$+NH3→R—C≡C—C≡C—Na+X—R'→R—C≡C—C≡C—R'

R and R' are alkyl groups and X is a halogen.

In this example, because the acetylide anion is a powerful nucleophile it may displace the halide ion from the primary alkyl halide to give a substituted dialkynyl as a product.

The term triple bond migration rearrangement also called an isomerization is the process by which one molecule is transformation into another molecule which has exactly the same atoms, but wherein these atoms are rearranged. When the isomerisation occurs intramolecularly it is considered a rearrangement reaction which is an organic reaction where the carbon skeleton of a molecule is rearranged to give a structural isomer of the original molecule. For example:

The term "hydrolysis" is used as the reverse or opposite of "condensation," a reaction in which two molecular fragments are joined for each water molecule produced. Thus, the two joined molecular fragments are reacted with water usually in the presence of an acid to break the fragments into separate fragments. A simple example is:

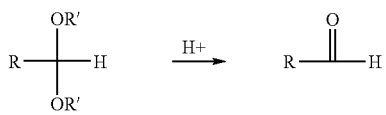

In this example R and R' are Alkyl.

The terms "cis" (Z) and "trans" (E) are also referred to as geometric stereoisomers with configurations relative to a C=C moiety. "Cis" also known as Z in nomenclature configures the carbons on a geometric plane to have the constituents of the substituted carbons on the same side of the plane as seen in the example of 2-butene. For example;

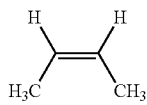

Conversely, "trans" also known as E in nomenclature configures the carbons on a geometric plane to have the on opposite sides of the plane as seen in the example of trans-2-butene. For example;

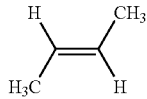

The term "environmentally benign" refers to using chemicals in synthetic reactions that create less of a burden on the environment. This includes but is not limited to the physical environment, the personal working environment, and the like. For example, for the physical environment, the issues in hazardous waste disposal of heavy metals and in the personal working environment, exposure to toxic chemicals being used or created by the worker or in odor concentration threshold nuisances.

The term "ambient temperature" is the normal temperature of the air and or environment around the process being performed usually between the temperature of 20° C. and 27° C. without any abnormal heat source being applied.

The term "starting material" is the compounds that are used to be reactants in each reaction step. This can be used interchangeably with intermediate products when it makes sense. For example, if a compound is having a reaction performed on it, it is a reactant and starting material. If a compound is the result of the reaction then it is not a starting material but could become a starting material if it is used in a subsequent reaction step.

The term "protecting group" is a chemical modification of a functional group moiety in order to obtain chemoselectivity in a subsequent chemical reaction of a multi-step organic synthesis. Conversely, when the protecting group is removed to allow for the functional group to be activated, this is called deprotection. For example, a compound with a terminal aldehyde is transformed into an acetal in order that the aldehyde is not available for synthetic modification in a subsequent synthetic step that could modify an un-protected aldehyde. After the subsequent synthetic step, the acetal is transformed back to the terminal aldehyde and is available as a functional group.

The terms "oxy" or "oxo" is an oxygen or a moiety that has a substituent of oxygen.

The terms "halo" and/or "halogen" refer to fluorine, chlorine, bromine or iodine.

The term "halide" is a binary compound, of which one part is a halogen atom and the other part is an element or radical that is less electronegative than the halogen, to make a fluoride, chloride, bromide, and iodide.

The term "acetal" refers to a carbon atom that is substituted with two single bonded oxygens such as an alkoxy moiety.

The term "aldehyde" refers to a terminal carbon atom bonded to a hydrogen atom and double bonded to an oxygen atom.

The term "alkyl" refers to a saturated aliphatic hydrocarbon radical including straight chain and branched chain groups of 1 to 16 carbon atoms. Examples of ($C_1$ to $C_6$) alkyl groups include methyl, ethyl, propyl, 2-propyl, n-butyl, iso-butyl, tert-butyl, pentyl, hexyl, and the like.

The term "alkenyl" means an alkyl moiety comprising 2 to 16 carbons having at least one carbon-carbon double bond. The carbon-carbon double bond in such a group may be anywhere along the 2 to 16 carbon chain that will result in a stable compound. Such groups could include both the E and Z isomers of said alkenyl moiety. Examples of such groups include, but are not limited to, ethenyl, propenyl, butenyl, allyl, and pentenyl.

As used herein, the term "alkynyl" means an alkyl moiety comprising from 2 to 16 carbon atoms and having at least one carbon-carbon triple bond. The carbon-carbon triple bond in such a group may be anywhere along the 2 to 16 carbon chain that will result in a stable compound. An "internal alkynyl" is when a triple bonded carbon pair is found at some position on the carbon chain that is not an end of the carbon chain. Conversely, a "terminal alkynyl" is when a triple bonded carbon pair is found at an end of the carbon chain. Examples of such groups include, but are not limited to, ethyne, propyne, 1-butyne, 2-butyne, 1-pentyne, 2-pentyne, 1-hexyne, 2-hexyne, and 3-hexyne.

The term "alkanal" means an alkyl moiety comprising 2 to 16 carbons having an aldehyde on a terminal end.

The term "alkenal" means an alkenyl moiety comprising of 2 to 16 carbons having an aldehyde on a terminal end.

As used herein, the term "diynyl" means an alkyl moiety comprising from 4 to 16 carbon atoms and having at least two carbon-carbon triple bonds. The carbon-carbon triple bond in such a group may be anywhere along the 4 to 16 carbon chain that will result in a stable compound.

The term "alkoxy", as used herein, means an O-alkyl group wherein said alkyl group contains from 1 to 16 carbon atoms and is straight, branched, or cyclic. Examples of such groups include, but are not limited to, methoxy, ethoxy, n-propyloxy, iso-propyloxy, n-butoxy, iso-butoxy, tert-butoxy, cyclopentyloxy, and cyclohexyloxy.

The term "cycloalkenyl" means an unsaturated, monocyclic ring structure having a total of from 5 to 8 carbon ring atoms with at least one C=C double bond in the cycle. Examples of such groups include, but not limited to, cyclopentenyl, cyclohexenyl.

According to one or more embodiments of the invention, methods of synthesis for the navel orangeworm pheromone are shown in FIG. 1, scheme 1. According to embodiments of the invention shown in FIG. 2, scheme 1a that generally follows pathway I of scheme 1, a step A is a reaction using compound of formula 1

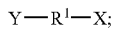 (1)

a step B is a reaction using compound of formula 2

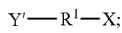 (2)

a step C is a reaction using compound of formula 3

 (3)

a step D is a reaction using compound of formula 5a

 (5a)

a step E is a reaction using compound of formula

 (4)

and using compound of formula 5b

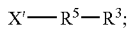 (5b)

a step F is a reaction using compound of formula 6

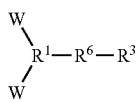 (5b)

to form the final compound of formula 7

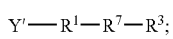 (7)

wherein: X and X' is halogen; Y is OH; Y is =O; $R^1$ is [—$CH_2$-]$_m$, alkyl; $R^2$ and $R^4$ are —C≡CH, alkynyl; $R^3$ is $CH_3$-[$CH_2$]$_n$—, alkyl; $R^5$ is [—C≡C-]$_p$, alkynyl, $R^6$ is [—C≡C-]$_q$, alkynyl $R^7$ is —C=C—C=C—, alkenyl, $R^8$, W is —O-alkyl, —O—$R^3$, —O—$CH_2$—$CH_3$; $R^8$ is the geometric cis configuration represented by structure

m is independently 5, 6, 7, 8, 9, 10, 11, 12; n is independently 1, 2, 3; p is independently 1, 2; and q is independently 1, 2.

Another embodiment of the invention is when X is chlorine; X' is bromine; $R^1$ is [—$CH_2$-]$_m$; $R^2$ is —C≡CH; $R^3$ is $CH_3$-[$CH_2$]$_n$—; $R^4$ is —C≡CH; $R^5$ is [—C≡C-]$_p$; $R^6$ is [—C≡C-]$_q$; $R^7$ is $R^8$; $R^8$ is the geometric cis configuration represented by structure

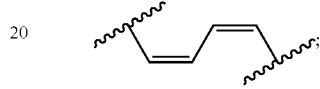

W is —O—$CH_2$—$CH_3$; m is 10; n is 1; p is 1; q is 2.

Figure 2:
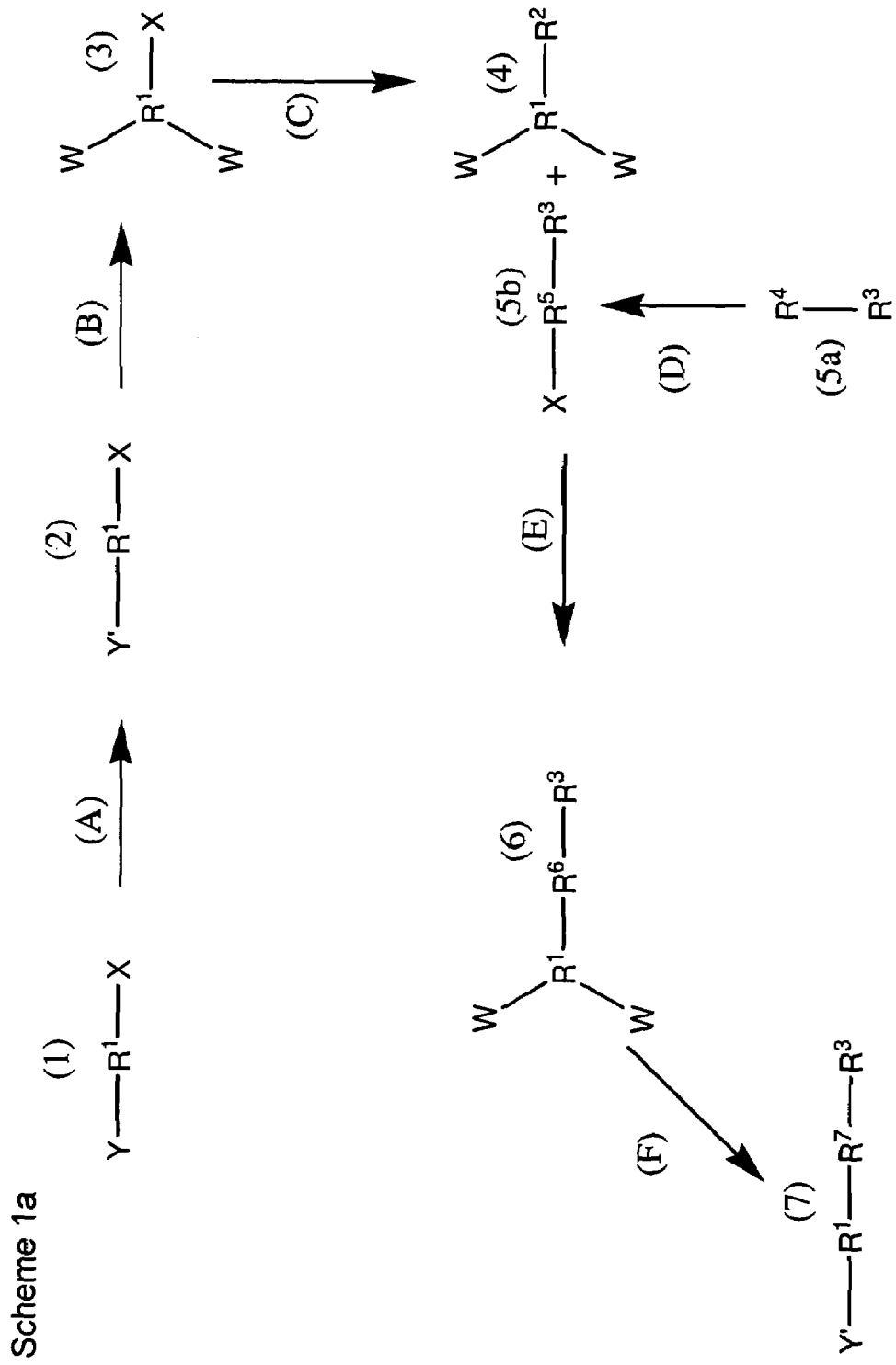
Figure 3:
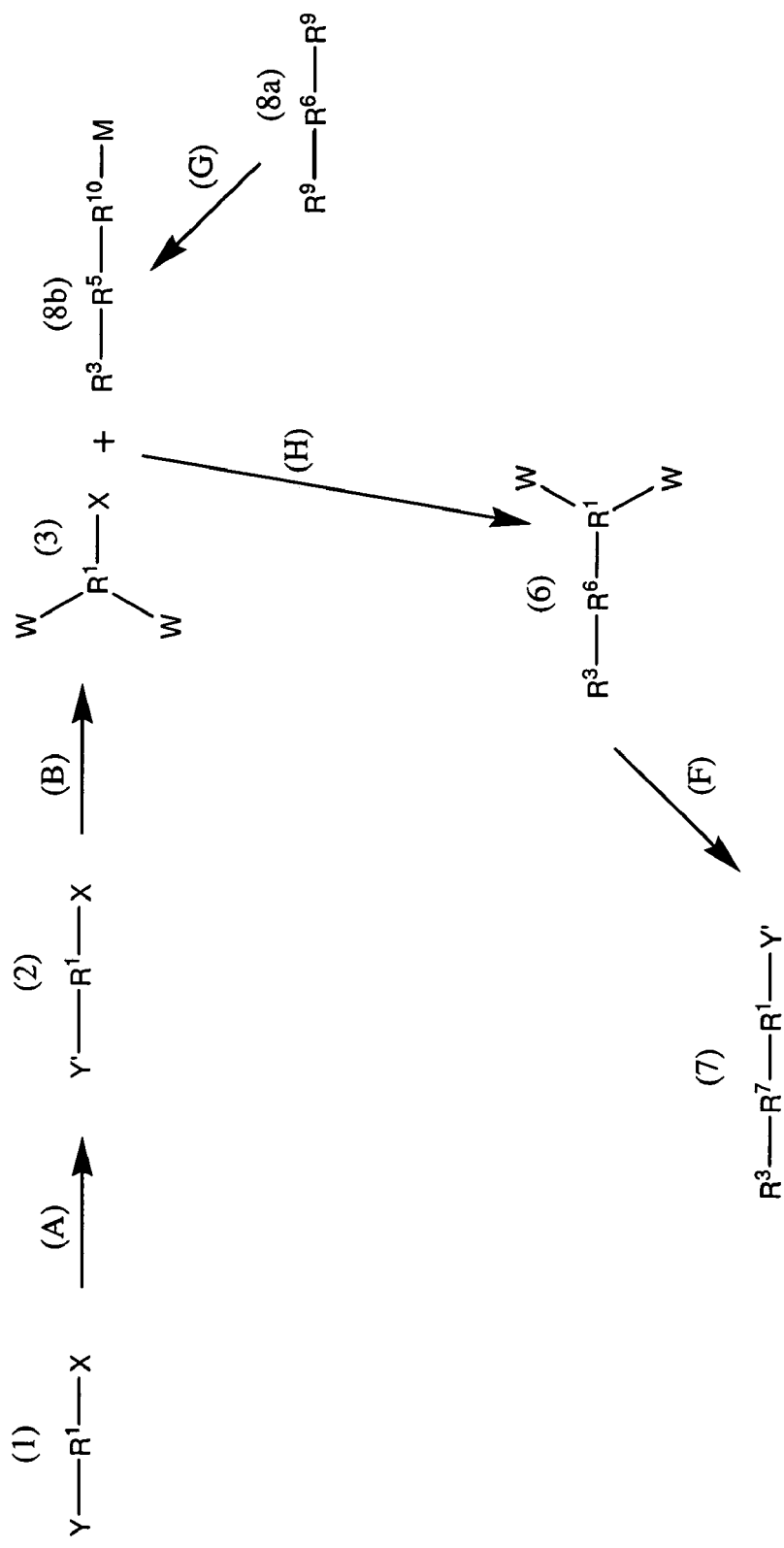
FIG. 3 is the outlined reaction scheme of the synthetic method shown in FIG. 1 Pathway II also named Scheme 1b.

In that the steps of FIG. 2, scheme 1a, and FIG. 3, scheme 1b, have similar overlapping steps, those steps have been given similar lettering and numbering for ease of following the synthetic pathways. Where the two pathways diverge other letters and numbers are used to show those sequence of steps. The alphabetical and numerical order is to be used as it makes sense in the schemes shown but is not necessarily in normal alphabetical or numerical order as seen in the pathways. According to the embodiments of the invention shown in FIG. 3, scheme 1b, that generally follows the pathway II of scheme 1, a step A is a reaction using compound of formula 1

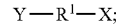 (1)

a step B is a reaction using compound of formula 2

 (2)

a step G is an optional reaction using compound of formula 8a

 (8a)

step H is a reaction using compound of formula 3

 (3)

and compound of formula 8b $R^3—R^5—R^{10}—M;$ (8b)

and step F is a reaction using compound of formula 6

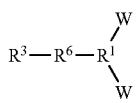

(6)

to form the final compound of formula 7

$$R^3—R^7—R^1—Y',$$ (7)

wherein: X is halogen; Y is —OH; Y' is ═O; R¹ is [—CH₂—]ₘ, or alkyl; R³ is CH₃-[CH₂]ₙ—, or alkyl; R⁵ is [—C≡C-]ₚ, or alkynyl; R⁶ is [—C≡C-]_q, or alkynyl; R⁷ is —C═C—C═C—, alkenyl, or R⁸; W is —O-alkyl, —O—R₃, or —O—CH₂—CH₃; R⁸ is the geometric cis configuration represented by structure

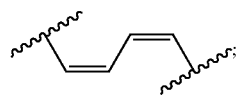

R⁹ is —CH₃, or alkyl; R¹⁰ is ═C⁽⁻⁾, carbon anion, or deprotonated carbon; M is a metal, such as but not limited to sodium, lithium, potassium, magnesium, wherein M and R¹⁰ together may form a salt; m is independently 5, 6, 7, 8, 9, 10, 11 or 12; n is independently 1, 2 or 3; p is independently 1 or 2; q is independently 1 or 2.

Another embodiment of the invention is when X is chlorine; R₁ is [—CH₂—]ₘ; R² is —C≡CH; R³ is CH₃-[CH₂]ₙ—; R⁵ is [—C≡C-]ₚ; R⁶ is [—C≡C-]_q; R⁷ is R⁸; W is —O—CH₂—CH₃; R⁸ is the geometric cis configuration represented by structure

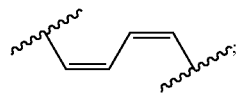

R⁹ is —CH₃, R¹⁰ is ═C⁽⁻⁾; M is sodium; m is 10; n is 1; p is 1; q is 2.

Other embodiments of the invention are described in the following steps.

Scheme 1: Step A:

In the method of synthesis shown in FIG. 1, scheme 1, according to embodiments of the invention, the compound of formula (1) which is generally known and commonly acquired is reacted to form compound of formula (2), preferably using an oxidation reaction and most preferably using a TEMPO oxidation. The compound of formula (1) is preferably a halo substituted alkyl alcohol, most preferably 10-chlorodecan-1-ol, and compound of formula (2) is preferably a halo substituted alkanal, most preferably 10-chlorodecan-1-al.

The method of synthesis shown in FIG. 1, scheme 1-step A according to embodiments of the invention is carried out using various diluents. Suitable diluents are virtually all inert organic solvents. These preferably include aliphatic, aromatic, and optionally halogenated hydrocarbons such as pentane, hexane, heptane, cyclohexane, petroleum ether, benzene, ligroin, benzene, toluene, xylene, methylene chloride, ethylene chloride, chloroform, carbon tetrachloride, chlorobenzene, and o-dichlorobenzene, ethers, such as diethyl ether, dibutyl ether, methyl-tert-butyl ether, methyl-tert amyl ether, glycol dimethyl ether and diglycol dimethyl ether, tetrahydrofuran, and dioxane; ketones such as acetone methyl ethyl ketone, methyl isopropyl ketone or methyl isobutyl ketone, esters, such as methyl acetate or ethyl acetate, nitriles, such as for example acetonitrile or propionitrile, amides such as for example, dimethylformamide, dimethylacetamide and N-methylpyrrolidone, and also dimethylsulfoxide, tetramethylene sulphone or hexamethyl phosphoric triamide. Most preferably the diluent is ethyl acetate.

The method of synthesis shown in FIG. 1, scheme 1, step A, according to embodiments of the invention is carried out using various reagents. Suitable reagents in the reaction are alkali halides such as for example sodium bromide, sodium chloride and sodium iodide, metal acetates, such as lithium, sodium or potassium acetate, preferably sodium acetate, and alkali metal hypochlorites, preferably sodium hypochlorite.

The method of synthesis shown in FIG. 1, scheme 1, step A, according to embodiments of the invention is carried out preferably using a catalyst, preferably cyclic nitrosyl tertiary amines, most preferably 2,2,6,6-Tetramethylpiperidinyloxy.

The reaction temperatures in method of synthesis of FIG. 1, scheme 1, step A, according to embodiments of the invention can be varied within a wide range. In general the step can be carried out between 0 and 35° C., preferably between 5 and 10° C.

The method of synthesis shown in FIG. 1, scheme 1, step A, according to embodiments of the invention is generally carried out under atmospheric pressure or slight positive pressure. However it is also contemplated that it is possible to operate under elevated or reduced pressures.

For carrying out the method of synthesis in FIG. 1, scheme 1, step A, according to embodiments of the invention, the reagents are generally in approximately equimolar amounts with the starting material. However, it is possible to have one or two of the reagents in either a small excess or shortage. The catalysts are generally in lower molar amounts as is necessary for the reaction. The work up is carried out by customary methods known in the art (cf. Example 1).

Scheme 1: Step B

In the method of synthesis shown in FIG. 1, scheme 1, according to embodiments of the invention, the compound of formula (2) is reacted to form compound of formula (3), preferably using an alkylation reaction, most preferably an O-alkyl-C-alkoxy addition reaction, particularly preferably an acetalization reaction. The compound of formula (2) is preferably a halo substituted alkanal, most preferably 10-chlorodecan-1-al and the compound of formula (3) is preferably a halo substituted dialkoxy substituted alkyl, most preferably 10-chloro-1,1-diethoxydecane.

The method of synthesis shown in FIG. 1, scheme 1, step B, according to embodiments of the invention is carried out using various diluents. Suitable diluents are virtually all inert organic solvents. These preferably include aliphatic, aromatic, and optionally halogenated hydrocarbons such as pentane, hexane, heptane, cyclohexane, petroleum ether, benzene, ligroin, benzene, toluene, xylene, methylene chloride, ethylene chloride, chloroform, carbon tetrachloride, chlorobenzene, and o-dichlorobenzene, ethers, such as diethyl ether, dibutyl ether, methyl-tert-butyl ether, methyl-tert amyl ether, glycol dimethyl ether and diglycol dimethyl ether, tetrahydrofuran, and dioxane; ketones such as acetone, methyl ethyl ketone, methyl isopropyl ketone or methyl isobutyl ketone, esters, such as methyl acetate or ethyl acetate, nitriles, such as for example acetonitrile or propionitrile, amides such as for example, dimethylformamide, dimethylacetamide and N-methylpyrrolidone, and also dimethylsulfoxide, tetramethylene sulphone or hexamethyl phosphoric triamide. Preferably the diluent of ethyl acetate.

The method of synthesis shown in FIG. 1, scheme 1, step B, according to embodiments of the invention is carried out using various reagents. Suitable reagents in the reaction are acetals such as chloroacetaldehyde dimethyl acetal, acetaldehyde dimethyl acetal, trimethyl orthoformate, trialkyl orthoformates most preferably triethylorthoformate, and alcohols such as methanol, ethanol, or isopropanol.

The method of synthesis shown in FIG. 1, scheme 1, step B, according to embodiments of the invention is carried out preferably using an acid catalyst, preferably organic acid, such as methanesulfonic acid or p-toluenesulfonic acid and most preferably p-toluenesulfonic acid.

The reaction temperatures in method of synthesis FIG. 1, scheme 1, step B, according to embodiments of the invention can be varied within a wide range. In general the step can be carried out between 0 and 60° C., preferably between 15 and 25° C., most preferably at ambient temperature.

The method of synthesis shown in FIG. 1, scheme 1, step B, according to embodiments of the invention is generally carried out under atmospheric pressure or slight positive pressure. However it is also contemplated that it is possible to operate under elevated or reduced pressures.

For carrying out the method of synthesis in FIG. 1, scheme 1-step B according to embodiments of the invention, the reagents are generally in approximately equimolar amounts with the starting material. However, it is possible to have the reagents in either a small excess or shortage. The catalysts are generally in lower molar amounts as is necessary for the reaction. The work up is carried out by customary methods known in the art (cf. Example 1).

Scheme 1: Pathway I, Step C

In the method of synthesis shown in FIG. 1, scheme 1, pathway I, step C, according to embodiments of the invention, the compound of formula (3) is reacted to form compound of formula (4), preferably using an alkylation reaction, more preferably an alkynyl-de-halogenation reaction. The embodiments of pathway I are also referred to as Scheme 1a. The compound of formula (3) is preferably a halo substituted dialkoxy substituted alkyl, most preferably 10-chloro-1,1-diethoxydecane and the compound of formula (4) is preferably a dialkoxy substituted alkynyl, most preferably 12,12-diethoxydodec-1-yne.

The method of synthesis shown in FIG. 1, scheme 1, pathway I, step C, according to embodiments of the invention is carried out using various diluents. Suitable diluents are virtually all inert organic solvents. These preferably include aliphatic, aromatic, and optionally halogenated hydrocarbons such as pentane, hexane, heptane, cyclohexane, petroleum ether, benzene, ligroin, benzene, toluene, xylene, methylene chloride, ethylene chloride, chloroform, carbon tetrachloride, chlorobenzene, and o-dichlorobenzene, ethers, such as diethyl ether, dibutyl ether, methyl-tert-butyl ether, methyl-tert amyl ether, glycol dimethyl ether and diglycol dimethyl ether, tetrahydrofuran, and dioxane; ketones such as acetone, methyl ethyl ketone, methyl isopropyl ketone or methyl isobutyl ketone, esters, such as methyl acetate or ethyl acetate, nitriles, such as for example acetonitrile or propionitrile, amides such as for example, dimethylformamide, dimethylacetamide and N-methylpyrrolidone, and also dimethylsulfoxide, tetramethylene sulfone or hexamethyl phosphoric triamide. Most preferably using diluent of dimethylsulfoxide.

The method of synthesis shown in FIG. 1, scheme 1, pathway I, step C, according to embodiments of the invention is carried out using various reagents. Suitable reagents in the reaction are organometallic acetylide complexes, preferably lithium acetylide, sodium acetylide and potassium acetylide complexes, most preferably lithium acetylide, ethylenediamine complex.

The method of synthesis shown in FIG. 1, scheme 1, pathway I, step C, according to embodiments of the invention is carried out preferably using a catalyst, most preferably a metal halide, particularly preferably sodium iodide.

The reaction temperatures in method of synthesis FIG. 1, scheme 1, pathway I, step C, according to embodiments of the invention can be varied within a wide range. In general the step can be carried out between 10 and 60° C., preferably between 20 and 40° C., most preferably at 30° C.

The method of synthesis shown in FIG. 1, scheme 1, pathway I, step C, according to embodiments of the invention is generally carried out under atmospheric pressure or slight positive pressure. However it is also contemplated that it is possible to operate under elevated or reduced pressures.

The yield from the method of synthesis FIG. 1, scheme 1, pathway I, step C, according to embodiments of the invention can be varied within a wide range. Preferably the range would be greater than 50%, most preferably the range would be greater than 76%, and particularly preferably the range would be greater than 90% and very particular preferably, greater than 93%.

For carrying out the method of synthesis in FIG. 1, scheme 1, pathway I, step C, according to embodiments of the invention, the reagents are generally in approximately equimolar amounts with the starting material. However, it is possible to have the reagents in either a small excess or shortage. The catalysts are generally in lower molar amounts as is necessary for the reaction. The work up is carried out by customary methods known in the art (cf. Example 1).

Scheme 1: Pathway I, Step D

In the method of synthesis shown in FIG. 1, scheme 1 according to embodiments of the invention, the compound of formula (5a) is reacted to form compound of formula (5b), preferably using a substitution reaction most preferably a halogenation. The compound of formula 5(a) is preferably an alkynyl, most preferably but-1-yne and compound of formula 5(b) is preferably a halo substituted alkynyl, most preferably 1-bromobut-1-yne.

The method of synthesis shown in FIG. 1, scheme 1, pathway I, step D, according to embodiments of the invention is carried out using various diluents. Suitable diluents are virtually all inert organic solvents. These preferably include aliphatic, aromatic, and optionally halogenated hydrocarbons such as pentane, hexane, heptane, cyclohexane, petroleum ether, benzene, ligroin, benzene, toluene, xylene, methylene chloride, ethylene chloride, chloroform, carbon tetrachloride, chlorobenzene, and o-dichlorobenzene, ethers, such as diethyl ether, dibutyl ether, methyl-tert-butyl ether, methyl-tert amyl ether, glycol dimethyl ether and diglycol dimethyl ether, tetrahydrofuran, and dioxane; ketones such as acetone, methyl ethyl ketone, methyl isopropyl ketone or methyl isobutyl ketone, esters, such as methyl acetate or ethyl acetate, nitriles, such as for example acetonitrile or propionitrile, amides such as for example, dimethylformamide, dimethylacetamide and N-methylpyrrolidone, and also dimethylsulfoxide, tetramethylene sulfone or hexamethyl phosphoric triamide. Preferably the diluent is water.

The method of synthesis shown in FIG. 1, scheme 1, pathway I, step D according to embodiments of the invention is carried out using various reagents. Suitable reagents in the reaction are alkali metal hydroxides, such as lithium hydroxide, sodium hydroxide, and potassium hydroxide, most preferably potassium hydroxide; and halogens such as chlorine, iodine, and bromine, preferably bromine or chlorine, most preferably bromine.

The reaction temperatures in method of synthesis FIG. 1, scheme 1, pathway I, step D, according to embodiments of the invention can be varied within a wide range. In general the step can be carried out between 10 and 85° C., preferably between 15 and 25° C., most preferably at ambient temperature.

The method of synthesis shown in FIG. 1, scheme 1, pathway I, step D, according to embodiments of the invention is generally carried out under atmospheric pressure or slight positive pressure. However it is also contemplated that it is possible to operate under elevated or reduced pressures.

For carrying out the method of synthesis in FIG. 1, scheme 1, pathway I, step D, according to embodiments of the invention, the reagents are generally in approximately equimolar amounts with the starting material. However, it is possible to have the halogen containing reagents in either a small excess or shortage and the metal hydroxide in great excess. The work up is carried out by customary methods known in the art (cf. Example 1).

Scheme 1: Pathway I Step E

In the method of synthesis shown in FIG. 1, scheme 1, pathway I, step E, according to embodiments of the invention, the compound of formula (5b) is reacted with the compound of formula (4) to form compound of formula (6), preferably using a cycle of oxidative additions and reductive eliminations, most preferably a Cadiot-Chodkiewicz reaction. The compound of formula (5b) is preferably a halo substituted alkynyl, most preferably 1-bromobut-1-yne and the compound of formula (4) is preferably a dialkoxy substituted alkynyl, most preferably 12,12-diethoxydodec-1-yne. The compound of formula (6) is preferably a dialkoxy substituted diynyl and most preferably 16,16-diethoxyhexadeca-3,5-diyne.

The method of synthesis shown in FIG. 1, scheme 1, pathway I, step E, according to embodiments of the invention is carried out using various diluents. Suitable diluents are virtually all inert organic solvents. These preferably include aliphatic, aromatic, and optionally halogenated hydrocarbons such as pentane, hexane, heptane, cyclohexane, petroleum ether, benzene, ligroin, benzene, toluene, xylene, methylene chloride, ethylene chloride, chloroform, carbon tetrachloride, chlorobenzene, and o-dichlorobenzene, ethers, such as diethyl ether, dibutyl ether, methyl-tert-butyl ether, methyl-tert amyl ether, glycol dimethyl ether and diglycol dimethyl ether, tetrahydrofuran, and dioxane; ketones such as acetone, methyl ethyl ketone, methyl isopropyl ketone or methyl isobutyl ketone, esters, such as methyl acetate or ethyl acetate, nitriles, such as for example acetonitrile or propionitrile, amides such as for example, dimethylformamide, dimethylacetamide and N-methylpyrrolidone, and also dimethylsulfoxide, tetramethylene sulfone or hexamethyl phosphoric triamide, alcohols such as methanol, ethanol, n-propanol, isopropanol, butanol, tert-butanol. Preferably the diluents of methanol and methyl-tert-butyl ether.

The method of synthesis shown in FIG. 1, scheme 1, pathway I, step E, according to embodiments of the invention is carried out using various reagents. Suitable reagents in the reaction are monoamines (primary or alkyl hydroxylamines), such as N-methyl or N-ethyl hydroxylamine most preferably hydroxylamine hydrochloride, and basic alkyl amines, such as ethylamine, triethylamine, propylamine, preferably n-propylamine.

The method of synthesis shown in FIG. 1, scheme 1, pathway I, step E, according to embodiments of the invention is carried out preferably using a catalyst, most preferably a metal halide, particularly preferably copper (I) chloride.

The reaction temperatures in method of synthesis FIG. 1, scheme 1, pathway I, step E, according to embodiments of the invention can be varied within a wide range. In general the step can be carried out between −40° C. and 25° C., preferably between 0 and −20° C., most preferably about 0° C. and about −20° C.

The method of synthesis shown in FIG. 1, scheme 1, pathway I, step E according to embodiments of the invention is generally carried out under atmospheric pressure or slight positive pressure. However it is also contemplated that it is possible to operate under elevated or reduced pressures.

For carrying out the method of synthesis in FIG. 1, scheme 1, pathway I-step E according to embodiments of the invention, the reagents are generally in excess in molar amounts with the starting material. The catalysts are generally in lower molar amounts as is necessary for the reaction. The work up is carried out by customary methods known in the art (cf. Example 1).

The yield from the method of synthesis FIG. 1, scheme 1, pathway I, step E according to embodiments of the invention can be varied within a wide range. Preferably the range would be greater than 50%, most preferably the range would be greater than about 76%, and particularly preferably the range would be greater than 87%.

Scheme 1: Pathway II Step G

In the method of synthesis shown in FIG. 1, scheme 1, pathway II, step G, is an optional step according to embodiments of the invention based on commercial availability of compound of formula (8b), needs of the synthesis and the like. The embodiments of pathway II are also referred to as Scheme 1b. The compound of formula (8a) is reacted to form compound of formula (8b), preferably using a triple bond migration rearrangement reaction, most preferably an isomerization. The compound of formula (8a) is preferably an internal alkyne, most preferably 2,4-hexadiyne and the compound of formula (8b) is preferably a terminal alkyne, most preferably, 1,3-hexadiyne.

The method of synthesis shown in FIG. 1, scheme 1, pathway II, step G, according to embodiments of the invention is carried out using various diluents. Suitable diluents are virtually all inert organic solvents. These preferably include aliphatic, aromatic, and optionally halogenated hydrocarbons such as pentane, hexane, heptane, cyclohexane, petroleum ether, benzene, ligroin, benzene, toluene, xylene, methylene chloride, ethylene chloride, chloroform, carbon tetrachloride, chlorobenzene, and o-dichlorobenzene, ethers, such as diethyl ether, dibutyl ether, methyl-tert-butyl ether, methyl-tert amyl ether, glycol dimethyl ether and diglycol dimethyl ether, tetrahydrofuran, and dioxane; ketones such as acetone, methyl ethyl ketone, methyl isopropyl ketone or methyl isobutyl ketone, esters, such as methyl acetate or ethyl acetate, nitriles, such as for example acetonitrile or propionitrile, amides such as for example, dimethylformamide, dimethylacetamide and N-methylpyrrolidone, and also dimethylsulfoxide, tetramethylene sulfone or hexamethyl phosphoric triamide. Most preferably using diluent of ether.

The method of synthesis shown in FIG. 1, scheme 1, pathway II, step G, according to embodiments of the invention is carried out using various reagents. Suitable reagents in the reaction are bases, such as strong bases of alkali metal amides sodium amide and potassium 3-aminoproylamide, preferably sodium amide.

The reaction temperatures in method of synthesis FIG. 1, scheme 1, pathway II, step G according to embodiments of the invention can be varied within a wide range. In general the step can be carried out between −10 and 50° C., preferably between 0 and 20° C., most preferably at 10° C.

The method of synthesis shown in FIG. 1, scheme 1, pathway II-step G according to embodiments of the invention is generally carried out under atmospheric pressure or slight positive pressure. However it is also contemplated that it is possible to operate under elevated or reduced pressures.

The yield from the method of synthesis FIG. 1, scheme 1, pathway II, step G according to embodiments of the invention can be varied within a wide range. Preferably the range would be greater than 50%, most preferably the range would be greater than 76%, and particularly preferably the range would be greater than 90%.

For carrying out the method of synthesis in FIG. 1, scheme 1, pathway II, step G, according to embodiments of the invention, the reagents are generally in approximately equimolar amounts with the starting material. However, it is possible to have the reagents in either a small excess or shortage. The work up is carried out by customary methods known in the art (see C. A. Brown and A. Yamashita (1975). "Saline hydrides and superbases in organic reactions. IX. Acetylene zipper. Exceptionally facile contrathermodynamic multipositional isomerization of alkynes with potassium 3-aminopropylamide". *J. Am. Chem. Soc.* 97 (4): 891-892).

Scheme 1: Pathway II Step H

In the method of synthesis shown in FIG. 1, scheme 1, pathway II, Step H, according to embodiments of the invention, the compound of formula (3) is reacted with compound of formula (8b) to form compound of formula (6), preferably using a nucleophilic addition reaction. The reaction is optionally performed in situ with the reactions of step G. The compound of formula (3) is preferably a halo substituted dialkoxy substituted alkyl, most preferably 10-chloro-1,1-diethoxydecane, the compound of formula (8b) is preferably a terminal alkynyl, most preferably, 1,3-hexadiyne, the compound of formula (6) is preferably a dialkoxy substituted diynyl and most preferably 16,16-diethoxyhexadeca-3,5-diyne.

The method of synthesis shown in FIG. 1, scheme 1, pathway II, step H, according to embodiments of the invention is carried out using various diluents. Suitable diluents are virtually all inert organic solvents. These preferably include aliphatic, aromatic, and optionally halogenated hydrocarbons such as pentane, hexane, heptane, cyclohexane, petroleum ether, benzene, ligroin, benzene, toluene, xylene, methylene chloride, ethylene chloride, chloroform, carbon tetrachloride, chlorobenzene, and o-dichlorobenzene, ethers, such as diethyl ether, dibutyl ether, methyl-tert-butyl ether, methyl-tert amyl ether, glycol dimethyl ether and diglycol dimethyl ether, tetrahydrofuran, and dioxane; ketones such as acetone, methyl ethyl ketone, methyl isopropyl ketone or methyl isobutyl ketone, esters, such as methyl acetate or ethyl acetate, nitriles, such as for example acetonitrile or propionitrile, amides such as for example, dimethylformamide, dimethylacetamide and N-methylpyrrolidone, and also dimethylsulfoxide, tetramethylene sulfone or hexamethyl phosphoric triamide. Preferably using diluent of ammonia, most preferably using a diluent of ether.

The method of synthesis shown in FIG. 1, scheme 1, pathway II, step H, according to embodiments of the invention is carried out using various reagents. Suitable reagents in the reaction are bases, such as strong bases of alkali metal amides, sodium amide, lithium amide, potassium amide, magnesium amide, and potassium 3-aminoproylamide, preferably sodium amide.

The reaction temperatures in method of synthesis FIG. 1, scheme 1, pathway II, step H, according to embodiments of the invention can be varied within a wide range. In general the step can be carried out between −10 and 50° C., preferably between 0 and 20° C., most preferably at 10° C.

The method of synthesis shown in FIG. 1, scheme 1, pathway II, step H, according to embodiments of the invention is generally carried out under atmospheric pressure or slight positive pressure. However it is also contemplated that it is possible to operate under elevated or reduced pressures.

The yield from the method of synthesis FIG. 1, scheme 1, pathway II, step H, according to embodiments of the invention can be varied within a wide range. Preferably the range would be greater than 50%, most preferably the range would be greater than 76%, and particularly preferably the range would be greater than 85%.

For carrying out the method of synthesis in FIG. 1, scheme 1, pathway II, step H, according to embodiments of the invention, the reagents are generally in approximately equimolar amounts with the starting material. However, it is possible to have the reagents in either a small excess or shortage. The work up is carried out by customary methods known in the art.

Scheme 1: Step F

In the method of synthesis shown in FIG. 1, scheme 1 according to embodiments of the invention, the compound of formula (6) is reacted to form the compound (7), preferably using a reduction reaction and a hydrolysis reaction, more preferably an alkyne reduction and an acetal hydrolysis. The compound of formula (6) is preferably a dialkoxy substituted diynyl, most preferably 16,16-diethoxyhexadeca-3,5-diyne and the compound of formula (7) is preferably a navel orangeworm sex attractant pheromone, most preferably the cis-cis isomer of the pheromone, and particularly preferably is (Z,Z)-11,13-hexadecadien-1-al.

The method of synthesis shown in FIG. 1, scheme 1, step F, according to embodiments of the invention is carried out using various diluents. Suitable diluents are virtually all inert organic solvents. These preferably include aliphatic, aromatic, and optionally halogenated hydrocarbons such as pentane, hexane, heptane, cyclohexane, petroleum ether, benzene, ligroin, benzene, toluene, xylene, methylene chloride, ethylene chloride, chloroform, carbon tetrachloride, chlorobenzene, and o-dichlorobenzene, ethers, such as diethyl ether, dibutyl ether, methyl-tert-butyl ether, methyl-tert amyl ether, glycol dimethyl ether and diglycol dimethyl ether, tetrahydrofuran, and dioxane; ketones such as acetone, methyl ethyl ketone, methyl isopropyl ketone or methyl isobutyl ketone, esters, such as methyl acetate or ethyl acetate, nitriles, such as for example acetonitrile or propionitrile, amides such as for example, dimethylformamide, dimethylacetamide and N-methylpyrrolidone, and also dimethylsulfoxide, tetramethylene sulfone or hexamethyl phosphoric triamide, Preferably the diluent is tetrahydrofuran.

The method of synthesis shown in FIG. 1, scheme 1, step F, according to embodiments of the invention is carried out using various reagents. Suitable reagents in the reaction are alkenes such as 2-methyl propene, 2-butene, 2-methyl butene and cycloalkenyls, such as cyclopentene, cyclohexene, cycloheptene and cyclooctene, most preferably cyclohexene; organometallic complexes, such as borane complexes, including borane-THF, borane-methylsulfide and borane-amine complexes, preferably borane-N,N-diethylaniline, a weak acid, such as formic acid, trifluoroacetic acid and acetic acid preferably glacial acetic acid; and either a strong aqueous acid, such as HCl or sulfuric acid, preferably sulfuric acid, or a metal tetrafluoroborate complex, such as copper (II) tetrafluoroborate or sodium borofluoride.

An unexpected benefit in using the preferred embodiment with borane-N,N-diethylaniline is the storage stability of the reagent, lack of nuisance odor and efficient reactions. While borane-THF is unstable with respect to storage past several months at ambient temperatures, DEANB is stable for long periods at ambient temperature. DEANB does not have a nuisance odor such as the case in using borane methyl sulfide. DEANB provides high yields of stereospecific product that is comparable or better than alternatives such as borane THF. DEANB as normally commercially available comes in a higher molar strength (5.6 M) than alternative boranes such as borane THF (1M) which allows more efficiency of utilizing higher concentrations in the reaction solution. Another efficiency is the reactivity of DEANB. This allows an almost stoichiometric amount of reagent (2:1) to be used to form the dicyclohexyl borane as compared to the borane THF which requires an excess.

According to embodiments of the invention in FIG. 1, scheme 1, step F, efficiencies are gained in the use of an organo metallic reducing agent in conjunction with hydrolysis agents such as a strong aqueous acid or metal fluoroborate complexes allowing for a combination of transformations in the compound with both a reduction in diynyls and hydrolysis of the acetal. Furthermore, use of the metal fluoroborate complexes allows for higher yields in the final transformation step.

The reaction temperatures in method of synthesis FIG. 1, scheme 1-step F according to embodiments of the invention can be varied within a wide range. In general the step can be carried out between −10° C. and 80° C., preferably between 5 and 60° C., most preferably about 5° C. and about 60° C.

The method of synthesis shown in FIG. 1, scheme 1-step F according to embodiments of the invention is generally carried out under atmospheric pressure or slight positive pressure. However it is also contemplated that it is possible to operate under elevated or reduced pressures.

For carrying out the method of synthesis in FIG. 1, scheme 1, step F, according to embodiments of the invention, the reagents are generally in excess in molar amounts with the starting material. The work up is carried out by customary methods known in the art (cf. Example 1). In the general work-up, the final product's separation or isolation from other synthetic constituents also known as purification can be carried out implementing common techniques such as concentration on silica gel, normal phase LC, reverse-phase HPLC, distillation or crystallization. A crystallization technique used for isolation may use a salt adducts such as sodium bisulfite. The purified final product can be held as a salt adduct to create a more stabile product. The salt adduct can subsequently be removed by application of a base. Crystallization can be advantageous because it does not apply heat, as in distillation, allowing for less degradation with thermally sensitive products.

The yield from the method of synthesis FIG. 1, scheme 1, step F, according to embodiments can be varied within a wide range. Preferably the range would be greater than 50%, most preferably the range would be greater than about 76%, and particularly preferably the range would be greater than 87%.

The method of synthesis according to embodiments of the inventions allows the final product to be used in the methods of trapping insects, methods for attracting insect pests, methods of disrupting mating as described in U.S. patent application 2006/0280765, and to be admixed with other pheromones from the Ando type I and type II categories for the same.

The method of synthesis according to embodiments of the invention allows for a synthesis kit which may include all necessary reagents as described herein, diluents as described herein, all intermediate and starting materials as described herein, and any necessary apparatuses to perform the reaction steps as described herein.

The following example of a specific embodiment for carrying out the invention is offered for illustrative purposes only and is not intended to limit the scope of the present invention in any way.

Procedures for the Examples

The structures and purities of the compounds of the following Examples were confirmed by proton magnetic resonance spectroscopy ($^1$H NMR) and gas chromatography (GC).

Proton magnetic resonance ($^1$H NMR) spectra were determined using a 300 megahertz, Varian Mercury System spectrometer operating at a field strength of 300 megahertz (MHz). Chemical shifts are reported in parts per million (ppm) downfield from an internal tetramethylsilane standard. Alternatively, $^1$H NMR spectra were referenced to residual protic solvent signal: $CHCl_3$=7.26 ppm. Peak multiplicities are designated as follows: s=singlet; d=doublet; dd=doublet of doublets; t=triplet; q=quartet, qn=quintet; br=broad resonance; and m=multiplet. Coupling constants are given in Hertz. GC chromatographs were run on a 5890 Series II Hewlett Packard System fitted with a SP™-2380 30 m×0.52 mm×0.20 μm column (SP) or HP-Ultra 2, 25 m×0.20 mm×0.33 μm column (HP). Unless otherwise stated, a gradient of 10° C./min starting at 40° C. held for 2 minutes moving the gradient for 25 minutes and bringing the temperature up to 250° C. for 2.0 minutes. Water content was estimated utilizing a Karl Fisher (KF) apparatus. Retention times (Rt) are given in minutes. All reactions were performed in septum-sealed flasks under a slight positive pressure of nitrogen, unless otherwise noted. All commercial reagents were used as received from their respective suppliers (Su). The following abbreviations are used herein: DEANB (borane-N,N-diethylaniline complex); NaBr (sodium bromide); NaOAc (sodium acetate) NaOCl (sodium hypochlorite); $NaHCO_3$ (sodium bicarbonate); $NaHSO_3$ (sodium bisulfite); NaI (sodium iodide); KOH (potassium hydroxide); $Br_2$ (bromine); $N_2$ (nitrogen); MTBE (methyl-tert-butyl ether), $HONH_2.HCl$ (hydroxylamine hydrochloride), CuCl (copper (I) chloride); $H_2SO_4$ (sulfuric acid), DMSO (dimethylsulfoxide); MeOH (methanol); THF (tetrahydrofuran); EtOAc (ethyl acetate); min. or min (minutes); h (hours).

Example 1

Figure 7:
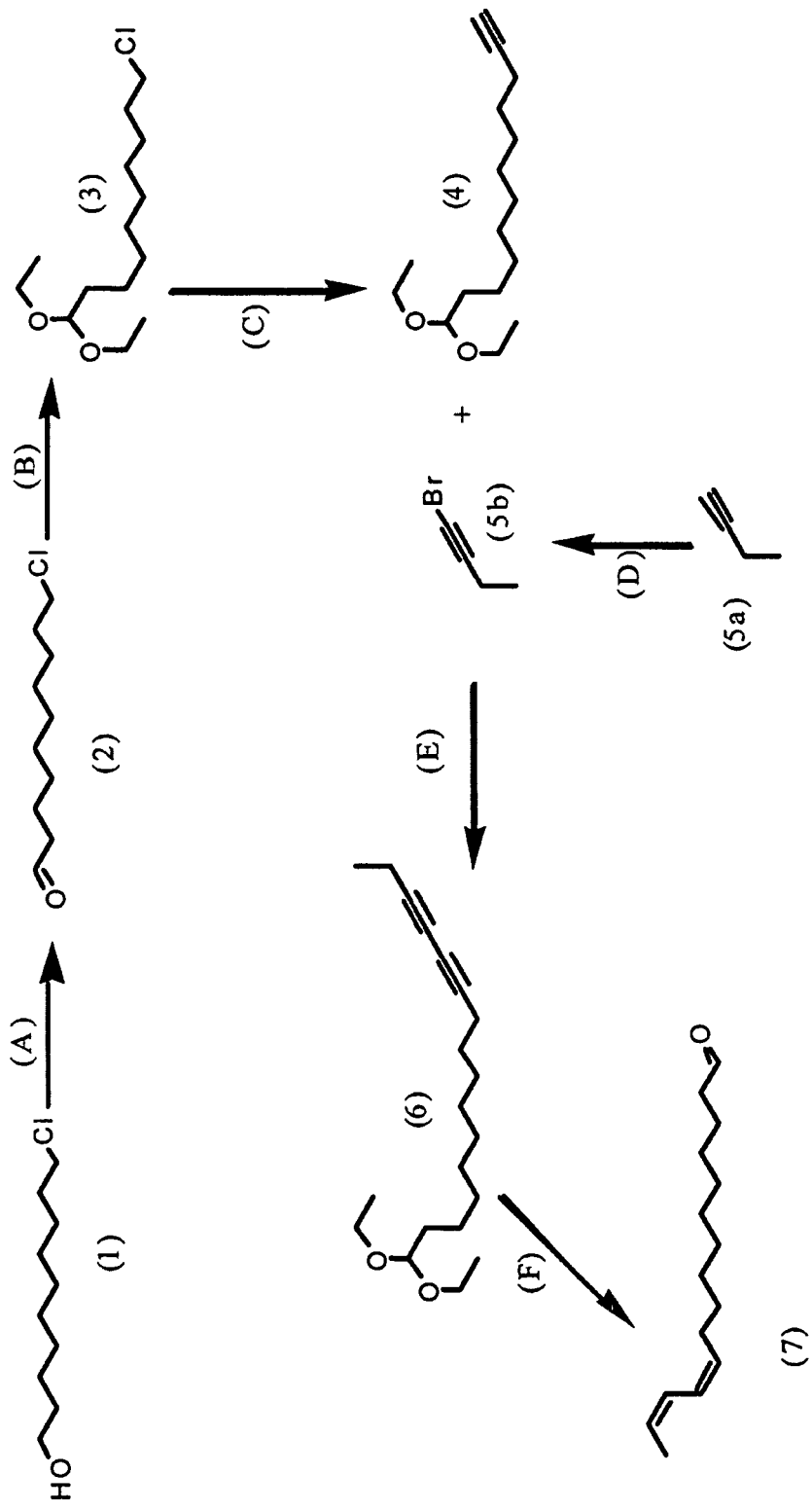
FIG. 7 is a synthetic scheme for Example 1.

See FIG. 7 for the general synthetic scheme for Example 1.

Example 1

Step A

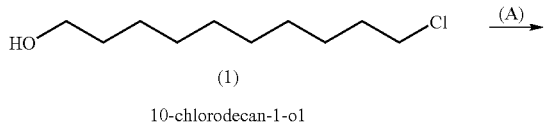

(1)

10-chlorodecan-1-ol

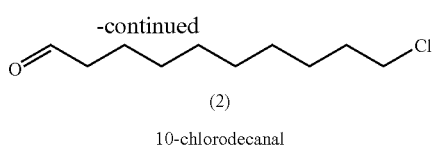

(2)

10-chlorodecanal

To a solution of 10-chlorodecanol 1 (20.0 g, 103.77 mMol, Su: Laviana (Lot: T-1094001), NaBr (8.33 g, 80.94 mMol, PA reagent, Su: Acros), NaOAc.3H$_2$O (21.18 g, 155.66 mMol, ACS reagent, Su: Aldrich) and 2,2,6,6-tetramethylpiperidinooxy (TEMPO) (162 mg, 1.04 mMol-(98% pure) Su: Acros) in H$_2$O (40 ml, tap) and EtOAc (120 ml, ACS reagent, Pharmco/AAPER) was added drop-wise NaOCl (100 ml, 115.19 mMol, 7.11% w/v solution Su: Aldrich) while maintaining internal temperature below 10° C. and mechanical stirring. Concentration of NaOCl was determined by titration. The reaction progress was monitored by GC and considered complete when <3A % of the starting alcohol 1 was remaining. After 2 hr stirring at 5° C., water (60 ml, H$_2$O, tap) was charged into the reaction mixture to quench the reaction, and aqueous NaHSO$_3$ (~1.0 ml, 2.0 M) was used to destroy remaining NaOCl if necessary. Check for remaining NaOCl with KI-starch test paper (Su: Fisher Scientific). Aqueous phase was extracted with EtOAc (50 ml) after phase separation. The combined organic layers were washed with H$_2$O (120 ml). The resulting organic phase was concentrated under reduced pressure (pot temperature ~35° C.) to a volume of ~50 ml. Fresh EtOAc (100 ml) was charged into it and then concentrated under reduced pressure (pot temperature ~35° C.) to the final volume of 50 ml. The water content of this resultant solution was checked by Karl Fisher method (repeat if necessary KF <0.4%), and the light-yellow solution was used without further purification. GC: column SP, starting condition 50° C. (1.0 min) then ramp to 250° C. at a rate of 10° C./min and hold at 250° C. for 1 minute, Rt=11.8 min for 10-chlorodecanol 1 and Rt=10.3 min for 10-chlorodecanal 2. $^1$H NMR (CDCl$_3$, 300 MHz): δ 9.77 (t, J=1.7 Hz, 1H), 3.53 (t, J=6.7 Hz, 2H), 2.43 (dt, J=7.5 Hz, J=1.7 Hz, 2H), 1.77 (qn, J=7.5 Hz, 2 Hz), 1.63 (m, J=7.2 Hz, 2H), 1.42 (m, J=7.2 Hz, 2H), 1.30 (br s, 8H).

Example 1

Step B

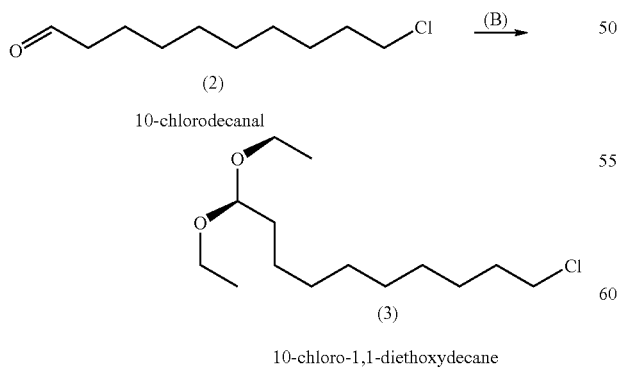

To the solution of 10-chlorodecanal 2 in EtOAc (50 ml, 103.77 mMol Su: from step A) at ambient temperature, under blanket of N$_2$, was charged p-toluenesulfonic acid monohydrate (200 mg, 1.04 mMol, (99%) Su: Acros) and triethylorthoformate (19 ml, 114.15 mMol (98%) Su: Acros). The reaction was monitored by GC for compound 2 consumption (compound 2<2.0 area % by GC). After 3 hr stirring at ambient temperature, a solution of H$_2$O (50 ml) and saturated NaHCO$_3$(aq.) (50 ml) was poured into the reaction mixture to quench the reaction. The aqueous layer was extracted with EtOAc (50 ml) after phase separation. The combined organic phases were washed with a solution of H$_2$O (50 ml) and brine (50 ml). The resulting organic phase was concentrated under reduced pressure (pot temperature ~35° C.) to a volume of 50 ml. Fresh EtOAc (100 ml) was charged into it and then concentrated under reduced pressure (pot temperature ~35° C.) to the final volume of 50 ml. The water content was checked by Karl Fisher method (repeat if necessary KF <0.4%). The resultant solution was concentrated under reduced pressure (pot temperature ~35° C.) until a constant weight (~28 g) was established. Resultant light yellow oil was used without further purification. GC: column SP, starting condition 50° C. (1.0 min) then ramp to 250° C. at a rate of 10° C./min and hold at 250° C. for 1 minute, Rt: 10.3 min for 10-chlorodecanal 2 and 9.9 min for 10-chloro-1,1-diethoxydecane 3. $^1$H NMR (CDCl$_3$, 300 MHz): δ 4.48 (t, J=5.93, 1H), 3.6 (m, J=7.03 Hz, 2H), 3.53 (t, J=6.8 Hz, 2H), 3.5 (q, J=7.03 Hz, 2H), 1.76 (qn, J=6.85 Hz, 2H), 1.6 (m, J=6.85 Hz, 2H), 1.4 (m, J=6.85 Hz, 2H), 1.29 (br s, 10H), 1.20 (t, J=7.03 Hz, 6H);

Example 1

Step C

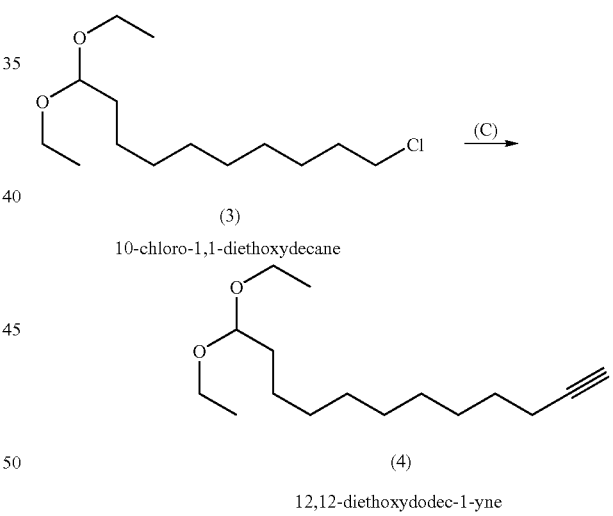

To a dark solution of lithium acetylide, ethylenediamine complex (13.8 g, 134.90 mMol, (90%) Su: Aldrich) and NaI (0.78 g, 5.19 mMol, (99+%), Su: Acros) in DMSO (100 ml anhydrous (99.7%) Su: Acros) was charged 10-chloro-1,1-diethoxydecane 3 (27.48 g, 103.77 mMol Su: from step B) while maintaining reaction temperature around 30° C., under a blanket of N$_2$. The addition funnel was rinsed with DMSO (15 ml, anhydrous, Su: Acros). The solution was monitored by GC for compound 3 consumption (compound 3<2.0 Area % by GC). After 4 hr stirring at 30° C., H$_2$O (200 ml) were charged into the reaction mixture to quench the reaction. The aqueous layer was extracted with heptane (2×200 ml). The organic layer was filtered through a plug of Celite® 521 (15 g, Su: Sigma-Aldrich) one by one after phase separation. The combined filtrate was washed with a solution of H₂O (100 ml) and brine (50 ml). The water in this organic solution was removed by azeotropic distillation under normal conditions by means of adding and removing heptane (repeat if necessary until KF=~0.2%). The resultant solution was concentrated under reduced pressure (pot temperature ~35° C.) to give 24.6 g of 12,12-diethoxydodec-1-yne 4 as an amber liquid (93% yield over steps A thru C, after C). This material was used without further purification. GC: column SP, Rt: 12.2 for 10-chloro-1,1-diethoxydecane 3, and Rt: 11.1 min for 12,12-diethoxydodec-1-yne 4 (<5 Area %). $^1$H NMR (CDCl₃, 400 MHz): δ 4.48 (t, J=5.60, 1H), 3.6 (m, J=7.07 Hz, 2H), 3.5 (m, J=7.07 Hz, 2H), 2.18 (dt, J=7.10, 2.80 Hz, 2H), 1.94 (t, J=2.60 Hz, 1H), 1.6 (m, 2H), 1.52 (qn, J=7.2 Hz, 2H), 1.4 (m, 2H), 1.29 (br s, 10H), 1.20 (t, J=7.00 Hz, 6H).

Example 1

Step D

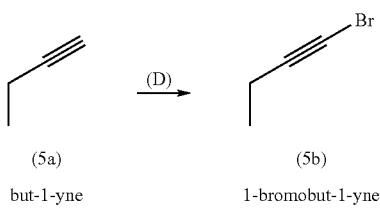

(5a) but-1-yne (5b) 1-bromobut-1-yne

To a solution of KOH (88.0 g, 1.57 Mole, flakes, 90+%, Su: Aldrich) in H₂O (400 ml, tap) was charged Br₂ (17.5 ml, 340 mMole, reagent grade, Su: Aldrich) at ambient temperature. Through this potassium bromide/bromate solution in Dreschel bottle (washing bottle) with fritted tube for gas dispersal was bubbled 1-butyne 5a (5.4 g, 99.83 mMol, 98+%, Su: Aldrich) at ambient temperature until the light yellow color of this aqueous solution turned colorless. The resultant aqueous solution was extracted with MTBE (200 ml, ACS reagent, Su: Pharmco/AAPER). After the separation of aqueous and organic layer, the organic solvents (~175 ml) were removed by normal distillation (temperature of distillate head: up to 60° C. and pot temperature: ~85° C.) to give a light yellow solution of 1-bromobutyne 5b in MTBE. GC: column HP, isocratic 35° C. (10 min), Rt: 4.92 min, $^1$H NMR (CDCl₃, 300 MHz): δ 2.22 (q, J=7.50, 2H), 1.15 (t, J=7.50 Hz, 3H);

Example 1

Step E

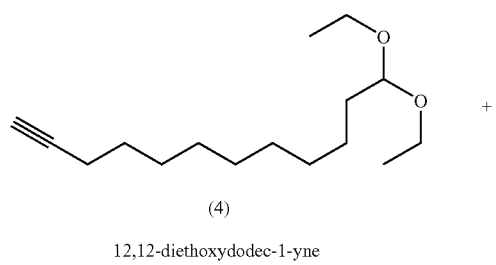

(4)
12,12-diethoxydodec-1-yne

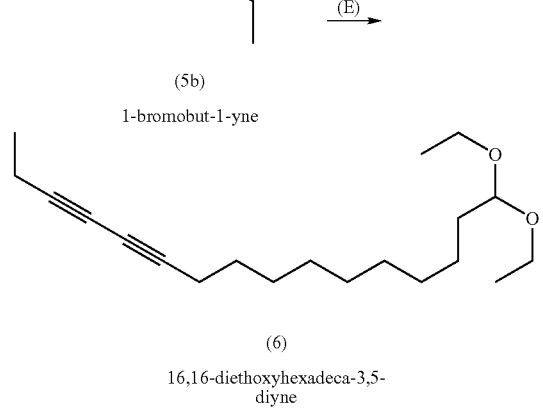

(5b)
1-bromobut-1-yne (6)
16,16-diethoxyhexadeca-3,5-diyne

To a suspension of hydroxylamine hydrochloride (7.6 g, 117.8 mMol, 99%, Su: Aldrich) and copper (I) chloride (0.39 g, 3.93 mMol, 97%, Su: Aldrich) in MeOH (80 ml, reagent ACS, Su: Pharmco/AAPER) at 0° C., under a blanket of N₂, was charged n-propylamine (20 ml, 243.27 mMoles, 98%, Su: Aldrich). After 15 min stirring, a solution of 12,12-diethoxydodec-1-yne 4 (10 g, 39.3 mMol, Su: from step C) in MeOH (10 ml) was charged and the addition funnel was rinsed with MeOH (5 ml). After 15 min stirring, the resulting clear solution was cooled down to −20° C. A solution of 1-bromobutyne 5b in MTBE (10.7 ml, 4.4 M, 47.2 mMol, Su: from step D) was added drop-wise within 3 hrs while maintaining temperature below −20° C. The reaction was monitored for the consumption of 12,12-diethoxydodec-1-yne 4 (<3.0 Area % by GC). After 2 hours, the resulting reaction mixture was directly extracted with heptane (3×200 ml). The extracted heptane-layer was passed through a pad of silica gel (10 g, gravity grade, Su: Silicycle). Solvent removed under reduced pressure to concentrate diyne 6 (10.5 g, 87% yield, 97.8 Area % by GC). This material was used without further purification. GC: column SP, Rt: 11.1 for 12,12-diethoxydodec-1-yne 4 (<3 Area %) and Rt: 16.8 for 16,16-diethoxyhexadeca-3,5-diyne 6. $^1$H NMR (CDCl₃, 300 MHz): δ 4.48 (t, J=5.85, 1H), 3.6 (m, J=7.10 Hz, 2H), 3.5 (m, J=7.10 Hz, 2H), 2.26 (m, J=7.50 Hz, 2H), 1.6 (m, 2H), 1.5 (m, 2H), 1.4~1.25 (br, 12H), 1.20 (t, J=7.05 Hz, 6H), 1.15 (t, J=7.50 Hz, 3H).

Example 1

Step F

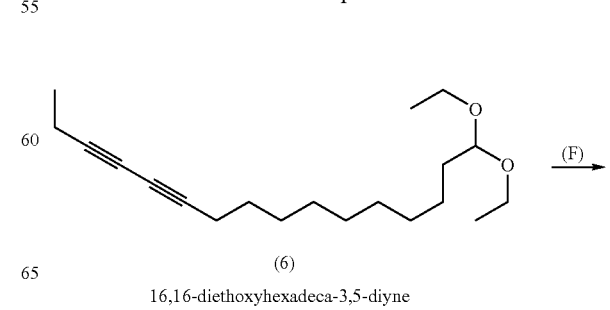

(6)
16,16-diethoxyhexadeca-3,5-diyne

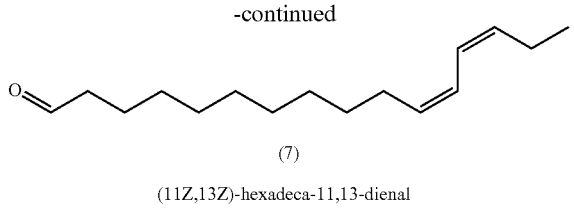

(7)

(11Z,13Z)-hexadeca-11,13-dienal

Figure 4:
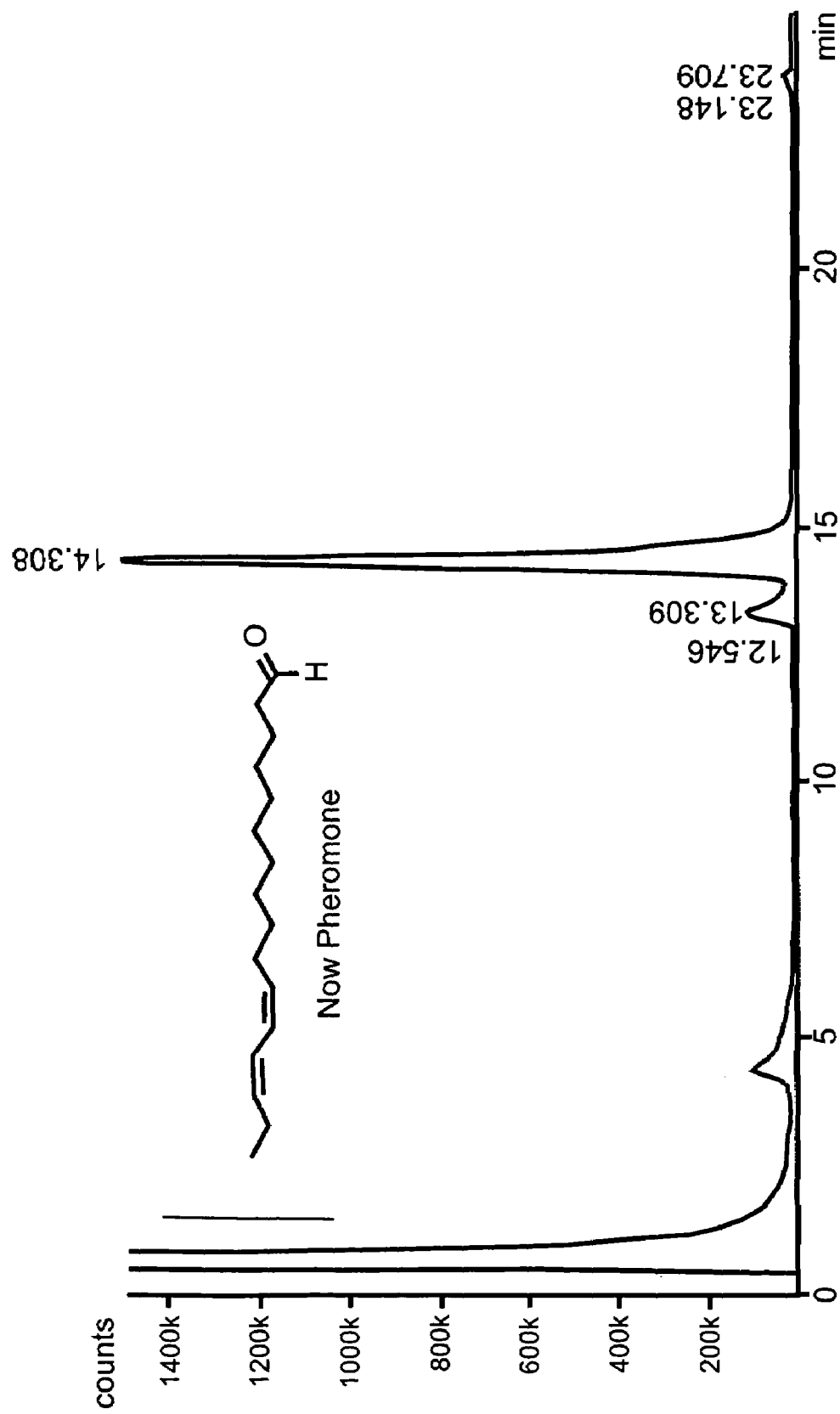
FIG. 4 is the GC chromatograph of the Example 1 compound 7 (Z,Z)-11,13-hexadecadienal.

To a solution of cyclohexene (10.6 ml, 104.84 mMol, 99%, Su: J-Star Research) in THF (20 ml {+/−0.2 ml}, distilled, Su: Pharmco/AAPER) was added DEANB (9.1 ml, 51.39 mMol, Su: Aldrich) at −5° C. under a blanket of $N_2$. After 2 hr stirring, 16,16-diethoxyhexadeca-3,5-diyne 6 (6.3 g, 20.56 mMol Su: from Step E) was charged while maintaining temperature ~5° C. Solution was monitored ~2.5 hrs at ~5° C. until clear. Solution was stirred 4 hr at ambient temperature. The solution was monitored by GC for the consumption of compound 6 (compound 6<2.0 Area % by GC). Glacial acetic acid (15.0 ml, 261 mMol, ACS grade, Su: Pharmco/AAPER) was charged. The solution was monitored after 4 hr stirring at ambient temperature until colorless. Aqueous sulfuric acid (100 ml, 4.0 M, Su: Aldrich) was charged, and the resulting solution was stirred at 60° C. for 2 hrs. After cooling to ambient temperature, the solution was extracted with heptane (2×100 ml). The combined organic layers were washed with $H_2O$ (100 ml) and saturated $NaHCO_3$(aq) (100 ml, Su: J-Star Research), respectively. A crude product (9.5 g) was obtained after solvent removal. This crude product was re-dissolved in heptane (100 ml) and stirred with $H_2O$ (100 ml). After 4 hr stiffing and phase separation, the organic layer was filtered through a pad of silica gel (6.3 g, gravity grade, Su: Silicycle) and concentrated to give crude compound 7 (5.4 g, 83% yield). Vacuum distillation gave compound 7 (1.55 g, 32% yield for this step) at 129~130° C./0.65 mmHg. GC: column SP, Rt: 14.3 min for (11Z,13,Z)-11,13-hexadecadien-1-al 7, 16.8 min for 16,16-diethoxyhexadeca-3,5-diyne 6 (<3 Area %) shown in FIG. 4. $^1$H NMR (CDCl$_3$, 300 MHz): δ 9.77 (t, J=1.95 Hz, 1H), 6.23 (m, 2H), 5.44 (m, 2H), 2.42 (dt, J=7.27, 1.80 Hz, 2H), 2.18 (m, 4H), 1.63 (m, J=7.35 Hz, 2H), 1.4-1.25 (broad, 12H), 1.00 (t, J=7.50 Hz, 3H).

Figure 5:
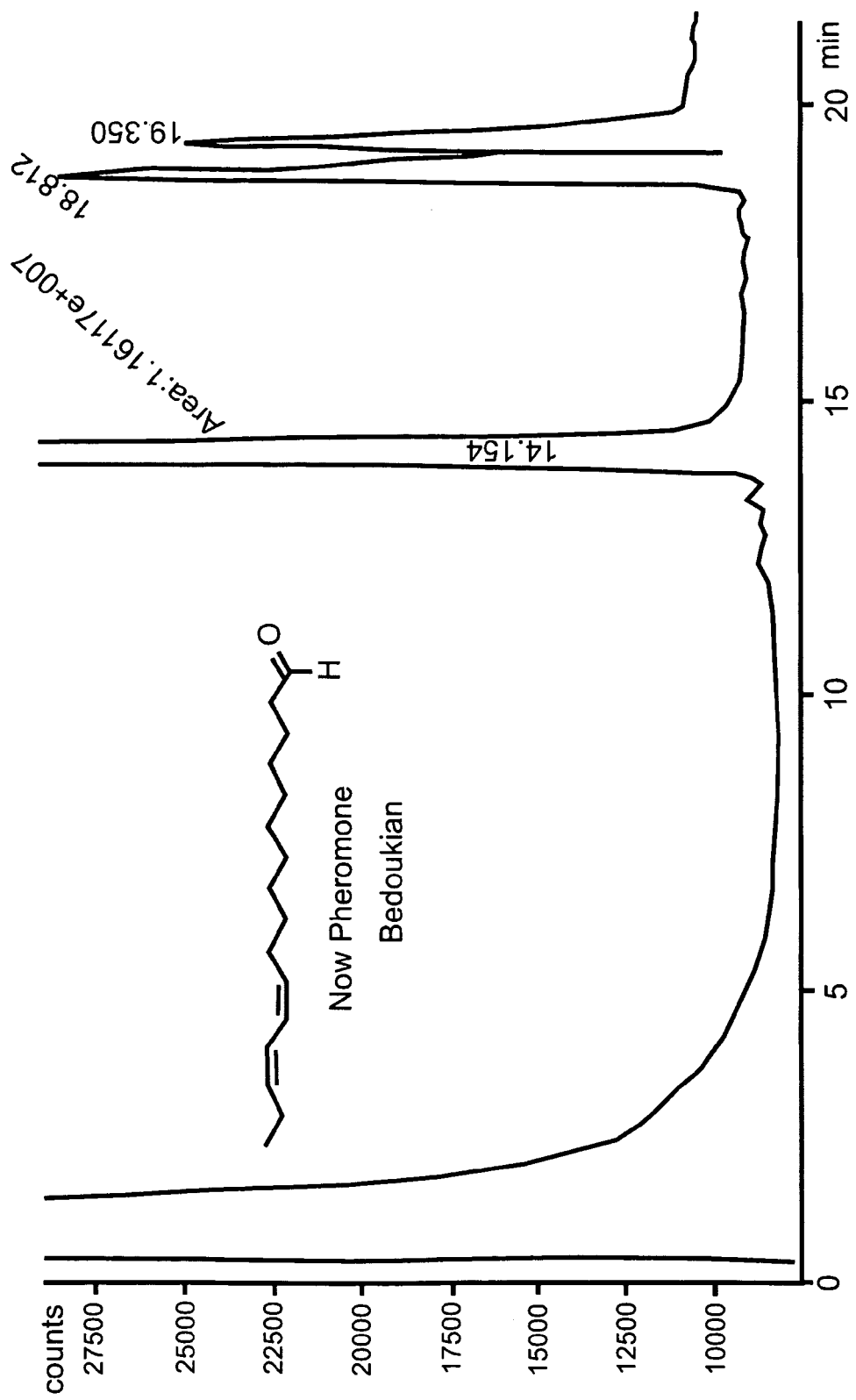
FIG. 5 is the GC chromatograph of a reference standard (Z,Z)-11,13-hexadecadienal.

Compound 7 obtained by the above synthesis was found to be identical to a standard navel orangeworm pheromone (Z,Z)-11,13-hexadecadien-1-al CAS number 71317-73-2 by GC shown in FIG. 5. and by $^1$H NMR.

While the invention has been described in terms of various embodiments, preferred embodiments, specific embodiments, specific examples, and applications thereof, the invention should be understood as not being limited by the foregoing detailed description, but as being defined by the appended claims and their equivalents. Numerous modifications and variations could be made thereto by those skilled in the art without departing from the scope of the invention set forth in the claims.

What is claimed is:

1. A method for synthesizing a (Z,Z)-11,13-hexadecadien-1-al consisting of the following steps:
    reacting a starting material 10-chlorodecan-1-ol with 2,2,6,6-tetramethylpiperidinyloxy in the presence of sodium bromide, sodium acetate and sodium hypochlorite in water and ethyl acetate to form a 10-chlorodecanal;
    reacting the 10-chlorodecanal with triethylorthoformate in the presence of paratoluene sulfonic acid in ethyl acetate to form a 10-chloro-1,1-diethoxydecane;
    optionally reacting a 2,4-hexadiyne with sodium amide in the presence of diethyl ether to form a 1,3-hexadiyne;
    reacting a 1,3-hexadiyne with the 10-chloro-1,1-diethoxydecane, in the presence of sodium amide and diethyl ether to form a 16,16-diethoxyhexadeca-3,5-diyne; and
    reacting the 16,16-diethoxyhexadeca-3,5-diyne with cyclohexene and borane-N,N-diethylaniline complex in THF, acetic acid, and a reagent selected from the group consisting of sulfuric acid, copper (II) tetrafluoroborate and sodium borofluoride to form the (Z,Z)-11,13-hexadecadien-1-al.

2. A method for synthesizing a sex attractant pheromone of formula 7 $R^3$—$R^7$—$R^1$—Y' (7) consisting of less than six synthetic steps, said six synthetic steps comprising:
    producing a compound of formula Y'—$R^1$—X (2) in step A, wherein step A comprises an oxidation reaction on a compound of formula Y—$R^1$—X (1);
    producing a compound of formula

(3)

(3) in step B, wherein step B comprises an alkylation reaction on (2) to; and
    producing a final compound of formula $R^3$—$R^7$—$R^1$—Y' (7) in step F, wherein step F comprises a reduction reaction and a hydrolysis reaction on an initial compound of formula

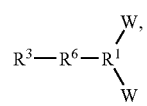

(6)

wherein:
    X is halogen,
    Y is —OH,
    Y' is =O,
    $R^1$ is [—$CH_2$—]$_m$, or alkyl,
    $R^3$ is $CH_3$-[$CH_2$]$_n$—, or alkyl,
    $R^5$ is [—C≡C-]$_p$, or alkynyl,
    $R^6$ is [—C≡C-]$_q$, or alkynyl,
    $R^7$ is —C=C—C=C—, alkenyl, or $R^8$,
    W is —O-alkyl, —O—$R_3$, or —O—$CH_2$—$CH_3$,
    $R^8$ is the geometric cis configuration represented by structure

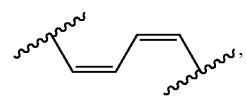

$R^9$ is —$CH_3$, or alkyl,
    $R^{10}$ is =$C_{(-)}$, carbon anion, or de-protonated carbon,
    M is a metal, sodium, lithium, potassium, or magnesium, wherein M and $R^{10}$ together may form a salt,
    m is independently 5, 6, 7, 8, 9, 10, 11 or 12,
    n is independently 1, 2 or 3,
    p is independently 1 or 2, and
    q is independently 1 or 2.

3. The method of claim 2, wherein said oxidation reaction of step A is an TEMPO oxidation.

4. The method of claim 2, wherein said alkylation reaction of step B is an O-Alkyl-C-alkoxy addition reaction.

5. The method of claim 2, wherein said reduction reaction and said hydrolysis reaction of step F is an alkyne reduction and an acetal hydrolysis.

6. The method of claim 2, wherein said six synthetic steps further comprise:
producing a compound of formula (6) in step H, wherein step H comprises reacting (3) with a compound of formula $R^3$-$R^5$-$R^{10}$-M (8b).

7. The method of claim 6, wherein step H comprises a nucleophilic addition reaction.

8. The method of claim 2, wherein said six synthetic steps further comprises:
producing a compound of formula

(4)

(4) in step C, wherein step C comprises an alkylation reaction on (3); and
producing a compound of formula (6) in step E, wherein step E comprises reacting (4) with a compound of formula $R^3$-$R^5$-X (5b).

9. The method of claim 8, wherein said alkylation reaction of step C is an alkynyl-de-halogenation reaction.

10. The method of claim 8, wherein step E comprises a cycle of oxidative additions and reductive eliminations.

11. The method of claim 8, wherein step E comprises a Cadiot-Chodkiewicz reaction.

12. The method of claim 2, wherein (1) comprises a halo substituted alkyl alcohol.

13. The method of claim 2, wherein (1) comprises 10-chlorodecan-1-ol.

14. The method of claim 2, wherein (2) comprises a halo substituted alkanal.

15. The method of claim 2, wherein (2) comprises 10-chlorodecanal.

16. The method of claim 2, wherein (3) comprises a halo substituted dialkoxy substituted alkyl.

17. The method of claim 2, wherein (3) comprises 10-chloro-1,1-diethoxydecane.

18. The method of claim 2, wherein (6) comprises a dialkoxy substituted diynyl.

19. The method of claim 2, wherein (6) comprises 16,16-diethoxyhexadeca-3,5-diyne.

20. The method of claim 2, wherein (7) is (Z,Z)-11,13-hexadecadien-1-al.

21. The method of claim 6, wherein (8b) comprises 1,3-hexadiyne.

22. The method of claim 6, wherein (8b) is synthesized from a compound of the formula $R^9$-$R^6$-$R^9$ (8a) through an isomerization reaction.

23. The method of claim 22, wherein (8a) comprises 2,4-hexadiyne.

24. The method of claim 8, wherein (5b) comprises 1-bromobut-1-yne.

25. The method of claim 8, wherein (5b) is synthesized from a compound of the formula $R^3$-$R^4$ (5a) through a halogenation reaction.

26. The method of claim 25, wherein (5a) comprises but-1-yne.

27. A method for synthesizing a (Z,Z)-11,13-hexadecadien-1-al consisting of the following steps:
reacting a starting material 10-chlorodecan-1-ol with 2,2,6,6-tetramethylpiperidinyloxy in the presence of sodium bromide, sodium acetate and sodium hypochlorite in water and ethyl acetate to form a 10-chlorodecanal;
reacting the 10-chlorodecanal with triethylorthoformate in the presence of para-toluene sulfonic acid in ethyl acetate to form a 10-chloro-1,1-diethoxydecane;
reacting the 10-chloro-1,1-diethoxydecane with lithium acetylide, ethylenediamine complex in presence of sodium iodide and dimethylsulfoxide to form a 12,12-diethoxydocdec-1-yne;
optionally reacting a but-1-yne with bromide in potassium hydroxide and water to form a 1-bromobut-1-yne,
reacting the 12,12-diethoxydocdec-1-yne in hydroxylamine hydrochloric acid and with copper (I) chloride in a n-propylamine methanol solution with the 1-bromobut-1-yne to form a 16,16-diethoxyhexadeca-3,5-diyne; and
reacting the 16,16-diethoxyhexadeca-3,5-diyne with cyclohexene and Borane-N,N-diethylaniline complex in THF and acetic acid and 4M sulfuric acid to form the (Z,Z)-11,13-hexadecadien-1-al.

* * * * *